US012416599B2

(12) United States Patent
Soleymani et al.

(10) Patent No.: US 12,416,599 B2
(45) Date of Patent: Sep. 16, 2025

(54) DIFFERENTIAL PHOTOELECTROCHEMICAL BIOSENSOR AND METHODS OF USE THEREOF

(71) Applicant: McMaster University, Hamilton (CA)

(72) Inventors: Leyla Soleymani, Oakville (CA); Sudip Saha, Hamilton (CA); Amanda Victorious, Oakville (CA)

(73) Assignee: McMaster University, Hamilton (CA)

( * ) Notice: Subject to any disclaimer, the term of this patent is extended or adjusted under 35 U.S.C. 154(b) by 922 days.

(21) Appl. No.: 17/572,376

(22) Filed: Jan. 10, 2022

(65) Prior Publication Data

US 2022/0221418 A1 Jul. 14, 2022

Related U.S. Application Data

(60) Provisional application No. 63/135,211, filed on Jan. 8, 2021.

(51) Int. Cl.
*G01N 27/30* (2006.01)
*C12Q 1/6825* (2018.01)
(Continued)

(52) U.S. Cl.
CPC ......... *G01N 27/305* (2013.01); *C12Q 1/6825* (2013.01); *G01N 27/127* (2013.01);
(Continued)

(58) Field of Classification Search
CPC ........ B82Y 30/00; B82Y 5/00; C12Q 1/6825; C12Q 2563/155; C12Q 2565/519;
(Continued)

(56) References Cited

U.S. PATENT DOCUMENTS

| 2018/0095067 | A1* | 4/2018 | Huff | G01N 33/48721 |
| 2020/0277664 | A1* | 9/2020 | Frenz | B01L 3/545 |
| 2022/0065806 | A1* | 3/2022 | Soleymani | G01N 27/3276 |

OTHER PUBLICATIONS

Victorious et al. Integrating TiO2 Nanoparticles within a Catecholic Polymeric Network Enhances the Photoelectrochemical Response of Biosensors. The Journal of Physical Chemistry, vol. 123, published Jun. 20, 2019, pp. 16186-16193.
(Continued)

*Primary Examiner* — Jennifer Wecker
(74) *Attorney, Agent, or Firm* — SMART & BIGGAR LP

(57) ABSTRACT

This disclosure relates to a biosensor, and methods of use thereof, for detecting a target in a sample comprising a photoelectrode comprising a conductive substrate and a photoactive material; a population of capture probes functionalized on the photoelectrode wherein the capture probes are capable of binding to the target and a reporter moiety; and the reporter moiety comprising a detectable label and a capture probe binding portion; wherein exposure of the target to the population of the capture probes results in binding of the target to a fraction of the population which results in a decrease in detection signal intensity compared to the intensity in the absence of the target, and subsequent binding of the reporter moiety to the remaining unbound capture probes results in an increase in detection signal intensity that is less than an increase from the reporter moiety binding to capture probes not exposed to the target.

20 Claims, 13 Drawing Sheets

Specification includes a Sequence Listing.

(51) Int. Cl.
- *G01N 27/12* (2006.01)
- *G01N 27/327* (2006.01)
- *H01G 9/20* (2006.01)
- *B82Y 5/00* (2011.01)
- *B82Y 30/00* (2011.01)

(52) U.S. Cl.
CPC ....... *G01N 27/3278* (2013.01); *H01G 9/2031* (2013.01); *B82Y 5/00* (2013.01); *B82Y 30/00* (2013.01)

(58) Field of Classification Search
CPC .............. G01N 27/127; G01N 27/305; G01N 27/3278; G01N 33/5438; H01G 9/2031
See application file for complete search history.

(56) References Cited

OTHER PUBLICATIONS

Grabar et al. Preparation and Characterization of Au Colloid Monolayers. Analytical Chemistry, vol. 67(4), published Feb. 15, 1995, pp. 735-743.

Zhang et al. A gold nanoparticle-based chronocoulometric DNA sensor for amplified detection of DNA. Nature Protocols, vol. 2(11), published online Nov. 8, 2007, pp. 2888-2895.

Steel et al. Electrochemical Quantitation of DNA Immobilized on Gold. Analytical Chemistry, vol. 70(22), published online Oct. 8, 1998, pp. 4670-4677.

Saha et al. Differential Photoelectrochemical Biosensing Using DNA Nanospacers to Modulate Electron Transfer between Metal and Semiconductor Nanoparticles. ACS Applied Materials and Interfaces, vol. 12, published Aug. 5, 2020, pp. 36895-36905.

Imani et al. Band edge engineering of TiO2@DNA nanohybrids and implications for capacitive energy storage devices. Nanoscale, vol. 7, first published May 7, 2015, pp. 10438-10448.

Ateş Sonmezoğlu et al. An Effective Approach for High-Efficiency Photoelectrochemical Solar Cells by Using Bifunctional DNA Molecules Modified Photoanode. Advanced Functional Materials, vol. 26, first published Nov. 9, 2016, pp. 8776-8783.

* cited by examiner

SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1
agggagatcg taagc                                                       15

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
tttttttttt gcttacgatc tccct                                            25

```
<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
tttttttttt tttttttttt ttttt                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
tttttttttt gcttacgatc tccct                                            25

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
tttttttttt gcatacgatc tccct                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
tttttttttt gcatacgatg tccct                                            25
```

DIFFERENTIAL PHOTOELECTROCHEMICAL BIOSENSOR AND METHODS OF USE THEREOF

RELATED APPLICATION

This disclosure claims benefit of U.S. Provisional Patent Application Ser. No. 63/135,211 filed Jan. 8, 2021, incorporated herein by reference in its entirety.

INCORPORATION OF SEQUENCE LISTING

A computer readable form of the Sequence Listing "P63768US01 Sequence Listing ST25" (1,423 bytes), submitted via EFS-WEB and created on Jan. 6, 2022, is herein incorporated by reference.

FIELD

The present disclosure relates to the field of biosensors and, in particular to, photoelectrochemical biosensors and methods of use thereof.

BACKGROUND

Photoelectrochemical (PEC) biosensors have been heavily explored over the past decade due to their promise for improved signal-to-noise ratio and enhanced limit-of-detection. These biosensors translate specific biorecognition events into a change in the output PEC signal. As with their electrochemical analogues, the limit-of-detection of PEC transducers is often compromised due to signal fluctuations caused by environmental interferents and minute variations in experimental conditions. In response, ratiometric or differential assays, combining two or more PEC signals, have been implemented to reduce the effect of interference and experimental variations, enhance detection accuracy at trace analyte concentrations, and improve analysis reliability.

Existing ratiometric PEC biosensors typically use multiple photoactive species—signal reporters or labels—that need to be activated at various voltages or wavelengths in order to obtain multiple signal readings for each biorecognition event. Although this multi-species approach is effective in increasing the signal-to-noise ratio of PEC biosensors, it increases the complexity of the measurement instrumentation and the calibration algorithms needed to deal with the varying baseline signals and chemical and optical stability observed when multiple photoactive materials are used in a single system.

The background herein is included solely to explain the context of the disclosure. This is not to be taken as an admission that any of the material referred to was published, known, or part of the common general knowledge as of the priority date.

SUMMARY

According to an aspect of the disclosure, provided herein is a biosensor for detecting a target analyte in a sample comprising:
  a) a photoelectrode comprising a conductive substrate and a photoactive material;
  b) a population of capture probes functionalized on the photoelectrode, wherein the capture probes are capable of binding to the target analyte and a reporter moiety; and
  c) the reporter moiety comprising a detectable label and a capture probe binding portion;
  wherein exposure of the target analyte to the population of the capture probes of b) results in binding of the target analyte to a fraction of the population of capture probes which results in a decrease in the intensity of detection signal compared to the intensity of detection signal in the absence of exposure of the target analyte,
  wherein the binding of the target analyte to a fraction of the population of capture probes of b) results in a population of remaining unbound capture probes, and
  wherein subsequent binding of the reporter moiety to the population of remaining unbound capture probes of c) results in an increase in intensity in detection signal that is less than an increase in intensity in detection signal from binding of the reporter moiety to a population of capture probes that has not been exposed to the target analyte.

In some embodiments, the detectable signal is a change in photoelectrochemical current, voltage or impedance. In some embodiments, the detectable signal is a change in photoelectrochemical current.

In some embodiments, the capture probe regulates distance between the detectable label and the substrate.

In some embodiments, the capture probe comprises a nucleic acid. In some embodiments, the capture probe comprises single-stranded DNA.

In some embodiments, the capture probe is smaller than or equal to the target analyte in size.

In some embodiments, the capture probe is smaller than or equal to the reporter moiety in size.

In some embodiments, the target analyte comprises a nucleic acid.

In some embodiments, the reporter moiety comprises a nucleic acid.

In some embodiments, the biosensor further comprises a surface blocker. In some embodiments, the surface blocker comprises monoethanolamine, mercaptohexanol and/or polyethylene glycol.

In some embodiments, the conductive substrate comprises metal, glass, polymer or a combination thereof.

In some embodiments, the conductive substrate comprises non-conductive glass or polymer and a conductive material. In some embodiments, the conductive material comprises indium tin oxide (ITO), fluorine-doped tin oxide (FTO), antimony-doped tin oxide (ATO), aluminum-doped zinc oxide (AZO), gallium-doped zinc oxide (GZO), indium-doped zinc oxide (IZO) or a combination thereof. In some embodiments, the polymer comprises polyethylene terephthalate (PET), polyethylene naphthalate (PEN), polyimide (PI), or a combination thereof.

In some embodiments, the conductive substrate comprises indium tin oxide.

In some embodiments, the photoactive material comprises thin films, photoactive particles, nanoparticles, microparticles, nanowires, nanorods, nanostars, nanomaterial, conductor materials, semiconductor materials, metals, metal oxides, carbon-based materials, conductive polymers, photoactive polymers, plasmonic materials, dyes, sulfide, metal chalcogenide, cadmium telluride, or a combination thereof In some embodiments, the metal oxide(s) are selected from the group consisting of Cd, Zn, In, Pb, Mo, W, Sb, Bi, Cu, Hg, Ti, Ag, Mn, Fe, V, Sn, Zr, Sr, Ga, Si, Cr, a perovskite such as $SrTiO_3$ or $CaTiO_3$, and a combination thereof.

In some embodiments, the metal chalcogenide is selected from the group consisting of CdSe, $In_2Se_3$, $WSe_2$, HgS, PbSe, CdTe, and a combination thereof.

In some embodiments, the photoactive material comprises titanium dioxide, zinc oxide, iron oxide, cadmium sulfide, cadmium telluride, or a combination thereof.

In some embodiments, the photoactive material comprises titanium dioxide.

In some embodiments, the titanium dioxide has a crystal structure that is at least one of anatase, rutile and brookite.

In some embodiments, the titanium dioxide is $P25\text{-}TiO_2$.

In some embodiments, the detectable label comprises a plasmonic nanoparticle, organic dye, light absorbing molecule, semiconductive nanoparticle, or a carbon-based nanomaterial.

In some embodiments, the detectable label comprises a metal, semiconductive quantum dot or organic semiconductor.

In some embodiments, the detectable label comprises a gold nanoparticle.

In accordance with another aspect, there is provided a device comprising the biosensor described herein.

In accordance with another aspect, there is provided a method of detecting a target analyte in a sample, the method comprising:
- a) contacting the sample with the photoelectrode of the biosensor disclosed herein under conditions for binding the target analyte to a fraction of the population of capture probes functionalized on the photoelectrode, wherein the binding of the target analyte to a fraction of the population of capture probes results in a population of remaining unbound capture probes;
- b) measuring a detectable signal generated from a);
- c) introducing the reporter moiety to the photoelectrode of the biosensor disclosed herein under conditions for binding the reporter moiety to the remaining unbound capture probes; and
- d) measuring a detectable signal generated from c);
  - wherein the binding of the target analyte to a fraction of the population of the capture probes in a) results in a decrease in the intensity of detection signal compared to the intensity of detection signal in the absence of any binding of the target analytes to the population of the capture probes;
  - wherein in c) introducing the reporter moiety to the photoelectrode results in the binding of the reporter moiety to the population of remaining unbound capture probes which results in an increase in intensity in detection signal that is less than an increase in intensity in detection signal from binding of the reporter moiety to a population of capture probes that has not been exposed and not bound to the target analyte; and
  - wherein a decrease in the signal intensity measured in b) from the capture probes binding the target analyte and an increase in the signal intensity measured in d) from the capture probes binding the reporter moiety indicates the presence of the target analyte in the sample.

In some embodiments, the detectable signal measured in b) is a change in photoelectrochemical current induced by the binding of the target analyte to the fraction of the population of the capture probes, and the detectable signal measured in d) is an additional change in photoelectrochemical current induced by the reporter moiety binding to the remaining unbound capture probes.

In some embodiments, the method further comprises calculating a difference and/or ratio between the detectable signal measured in b) from the capture probes binding the target analyte and measured in d) from the capture probes binding the reporter moiety.

In some embodiments, the sample comprises tissue samples, urine, blood, serum, other bodily fluids and/or secretions.

In accordance with another aspect, there is provided a kit for detecting a target analyte in a sample, wherein the kit comprises the biosensor described herein and instructions for use.

In accordance with another aspect, there is provided a kit for detecting a target analyte in a sample, wherein the kit comprises components required for the method described herein and instructions for use of the kit.

In accordance with another aspect, there is provided use of the biosensor described herein to determine the presence of a target analyte in a sample.

In accordance with another aspect, there is provided use of the kit described herein to determine the presence of a target analyte in a sample.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

Certain embodiments of the disclosure will now be described in greater detail with reference to the attached drawings in which:

FIG. 1A shows the operation of the differential photoelectrochemical biosensor in exemplary embodiments of the disclosure. FIG. 1A show a schematic illustration depicting the development of the PEC biosensor with the expected change in photocurrent profile depicted at each stage of sensing. A scanning electron micrograph (SEM) demonstrates the photoelectrode surface structure (bottom left). (i) Baseline photoelectrodes are created via solution deposition of $TiO_2$ NPs onto ITO substrates, yielding an anodic photocurrent upon 405 nm illumination. (ii) Biofunctionalized photoelectrodes are created by depositing 15-mer DNA probes on photoactive $TiO_2$ substrates, yielding a decrease in photocurrent. (iii) 25-mer nucleotide targets are hybridized onto the transducer, resulting in a further decrease in photocurrent. (iv) Introducing signal amplifying barcodes (SABs) gives rise to an amplified photocurrent following hybridization.

FIG. 1B shows the operation of the differential photoelectrochemical biosensor in exemplary embodiments of the disclosure. FIG. 1B shows a depiction of the combination of signals following target and SAB hybridization to yield the differential signal processing scheme used herein.

FIG. 2 shows chronocoulometric measurement of probe density in an exemplary embodiment of the disclosure. Circles represent the data obtained by running the scan with 10 mM Tris-buffer and squares represent the data obtained by running the scan with 100 µM hexaammineruthenium (III) chloride in 10 mM Tris-buffer (Tris+Ruhex). Corresponding solid lines indicate the linear fit that was used to obtain the y-axis intercept.

FIG. 3A shows photoelectrochemical signal generation on the differential DNA biosensor in exemplary embodiments of the disclosure. FIG. 3A shows a schematic showing the mechanism for photocurrent generation (i) bare $TiO_2$ electrode (ii) after hybridization with complementary target (iii) after hybridization with SAB.

FIG. 3B shows photoelectrochemical signal generation on the differential DNA biosensor in exemplary embodiments of the disclosure. FIG. 3B shows photocurrent measurement after each step of the biosensor operation with 1 pM target in buffer using a 405 nm LED as excitation source at 160 W/m². All photocurrent measurements were performed at 0 V bias vs. Ag/AgCl using 0.1 M ascorbic acid (AA) in 0.1 M PBS as electrolyte at each step of the biosensor construction.

FIG. 3C shows photoelectrochemical signal generation on the differential DNA biosensor in exemplary embodiments of the disclosure. FIG. 3C shows electrochemical impedance spectroscopy measurements performed in dark at open circuit potential vs. Ag/AgCl reference electrode using 2 mM $[Fe(CN)_6]^{3-/4-}$ in 0.1 M PBS and 0.1 M KCl as electrolyte. The equivalent circuit based on the shape of the Nyquist diagram is shown in the inset. Charge transfer resistance between the redox couple and the electrode is denoted by Rct, which can be determined from the diameter of the semicircle. $R_s$, $Z_w$ and CPE denote the solution resistance, Warburg impedance and constant phase element, respectively.

FIG. 6A shows photocurrent measurements performed at 0 V versus Ag/AgCl in 0.1 M ascorbic acid in 0.1 M PBS as electrolyte, illuminated using a 405 nm LED excitation source at 160 W/m² PEC graphs demonstrate signal responses following target and SAB binding in PBS.

Figure 6A:
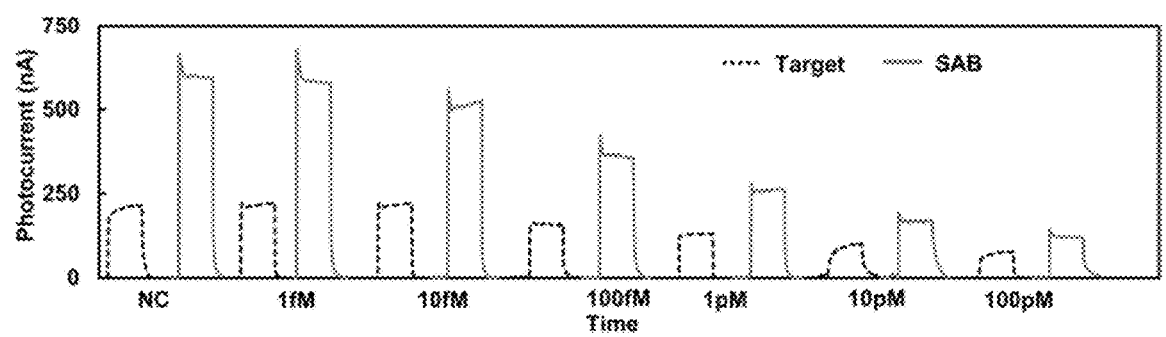
FIG. 6A shows limit-of-detection and sensitivity of the differential assay in exemplary embodiments of the disclosure.
Figure 6B:
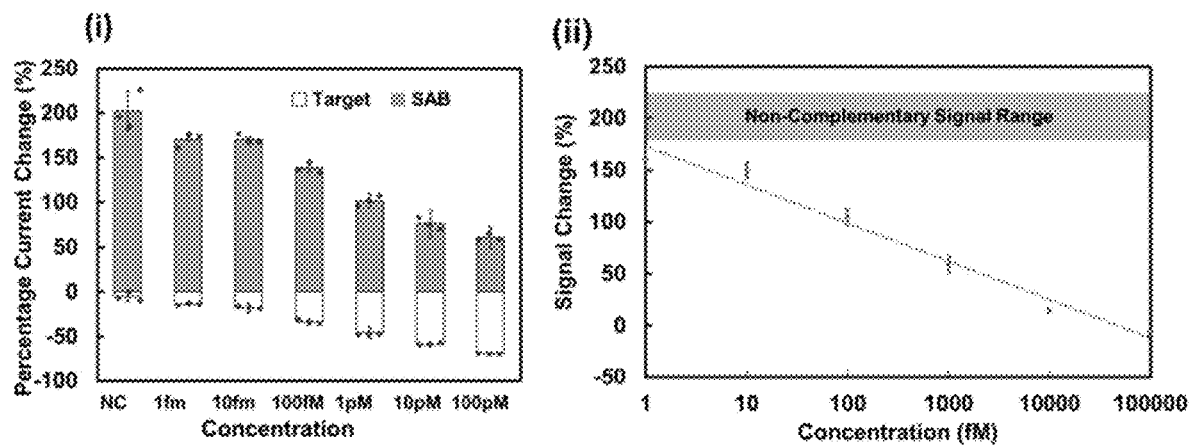

FIG. 6B shows limit-of-detection and sensitivity of the differential assay in exemplary embodiments of the disclosure. FIG. 6B shows Jitter plots (i) demonstrating the signal changes obtained from target and SAB binding in buffer obtained from results shown in FIG. 6A. Representation of the differential signal (ii) obtained from the data presented in (i). The linear region of the calibration curve of the PBS graph was fitted using the equation $\Delta I \% = -49 \log^{10} C + 173$ (correlation coefficient of 97.97%).

Figure 6C:
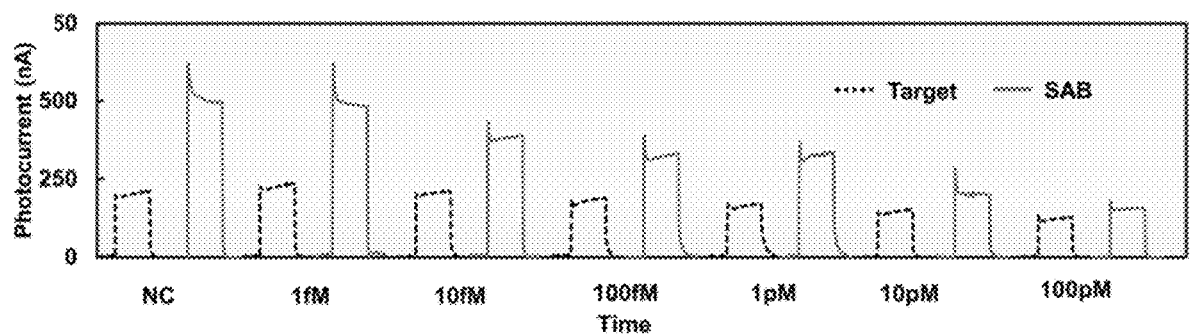

FIG. 6C shows limit-of-detection and sensitivity of the differential assay in exemplary embodiments of the disclosure. FIG. 6C shows photocurrent measurements performed at 0 V versus Ag/AgCl in 0.1 M ascorbic acid in 0.1 M PBS as electrolyte, illuminated using a 405 nm LED excitation source at 160 W/m² PEC graphs demonstrate signal responses following target and SAB binding in urine.

Figure 6D:
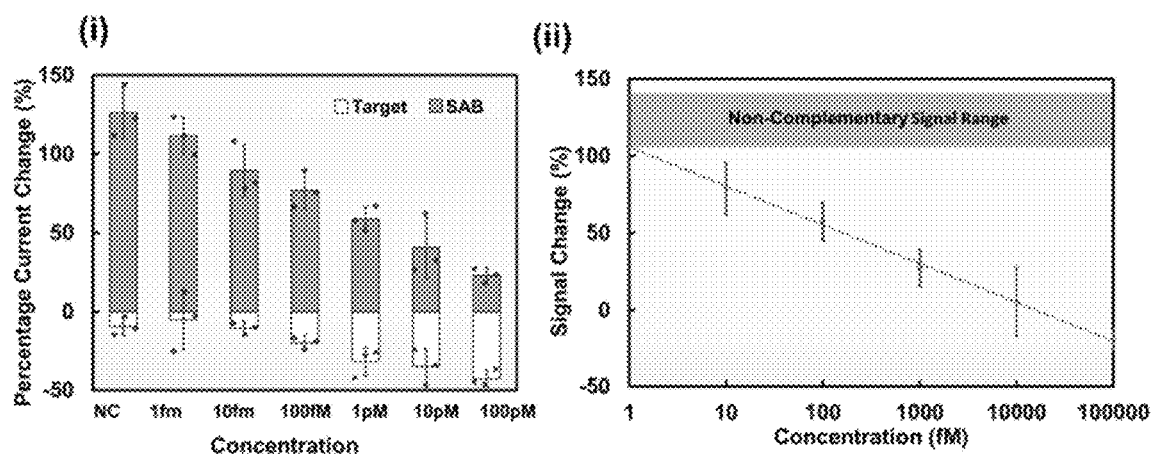

FIG. 6D shows limit-of-detection and sensitivity of the differential assay in exemplary embodiments of the disclosure. FIG. 6D shows Jitter plots (i) demonstrating the signal changes obtained from target and SAB binding in urine, obtained from results shown in FIG. 6C. Representation of the differential signal (ii) obtained from the data presented in (i). The equation $\Delta I \% = -25 \log_{10} C + 106$ (correlation coefficient of 99.84%) was used to fit the urine data.

Figure 7:
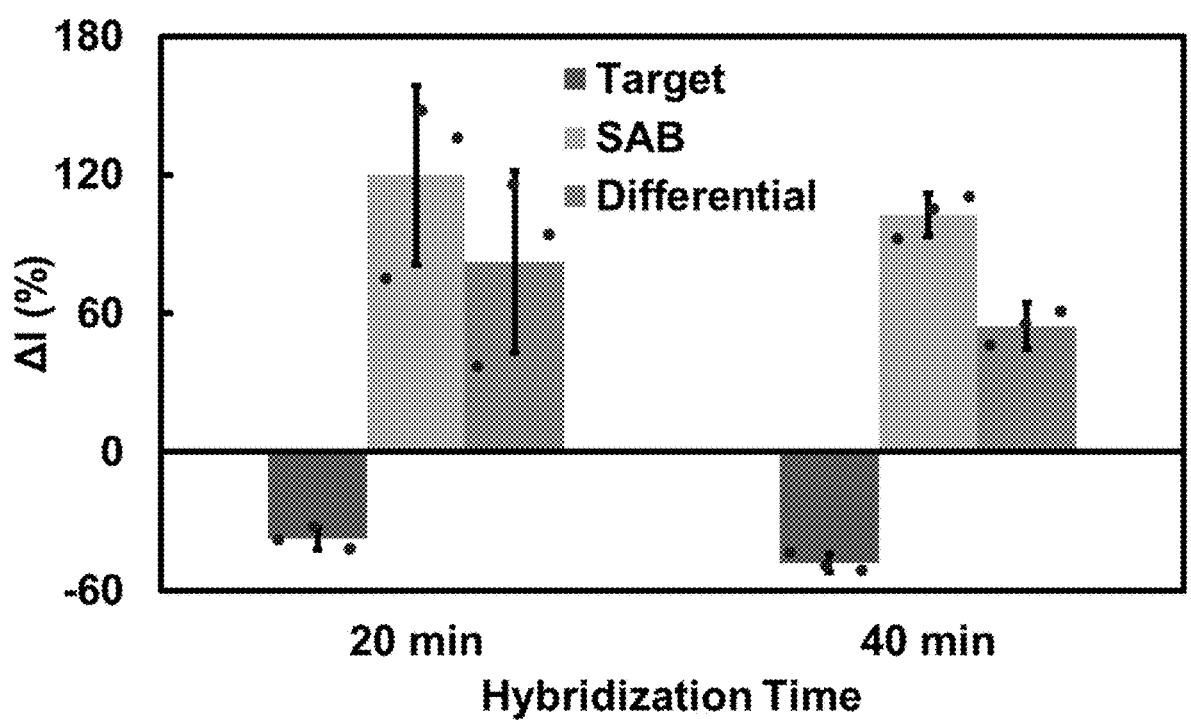

FIG. 7 shows a comparison of photocurrent change in detecting 1 pM DNA targets spiked in buffer (PBS) at 20-minute and 40-minute hybridization times in an exemplary embodiment of the disclosure. The error bars indicate one standard deviation from the mean and calculated from at least three measurements performed at 0 V versus Ag/AgCl in 0.1 M ascorbic acid in 0.1 M PBS as electrolyte, illuminated using a 405 nm LED excitation source at 160 W/m².

Figure 8A:
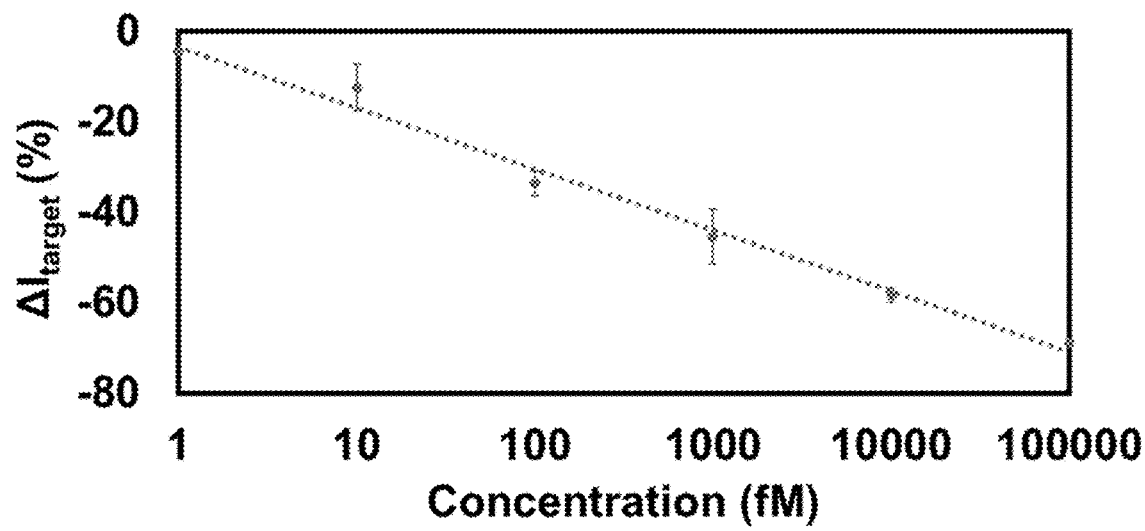

FIG. 8A shows limit-of-detection of the signal-off-detection mode in PBS in an exemplary embodiment of the disclosure.

Figure 8B:
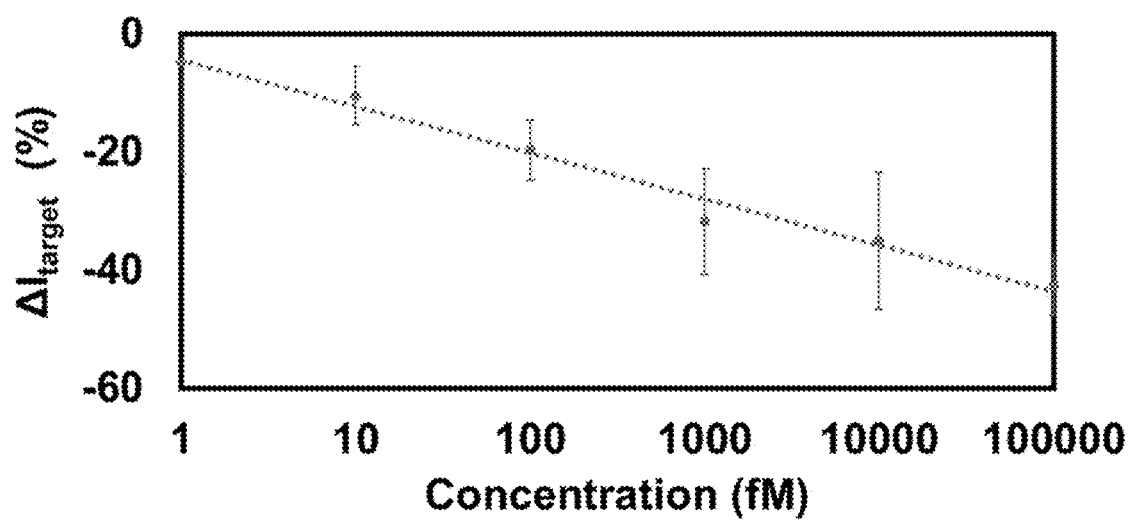
Figure 9:
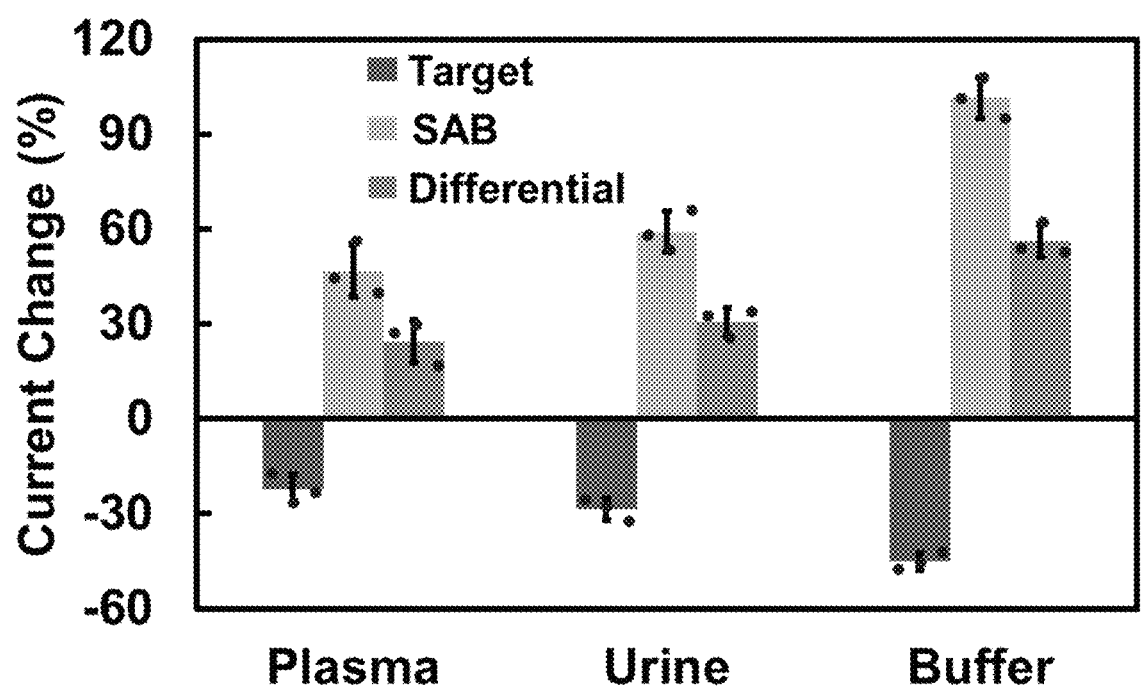

FIG. 8B shows limit-of-detection of the signal-off-detection mode in urine in an exemplary embodiment of the disclosure FIG. 9 shows signal changes measured with 1 pM DNA target spiked into human plasma, urine, and buffer in an exemplary embodiment of the disclosure. The error bars indicate one standard deviation from the mean, calculated from at least three measurements.

Figure 10A:
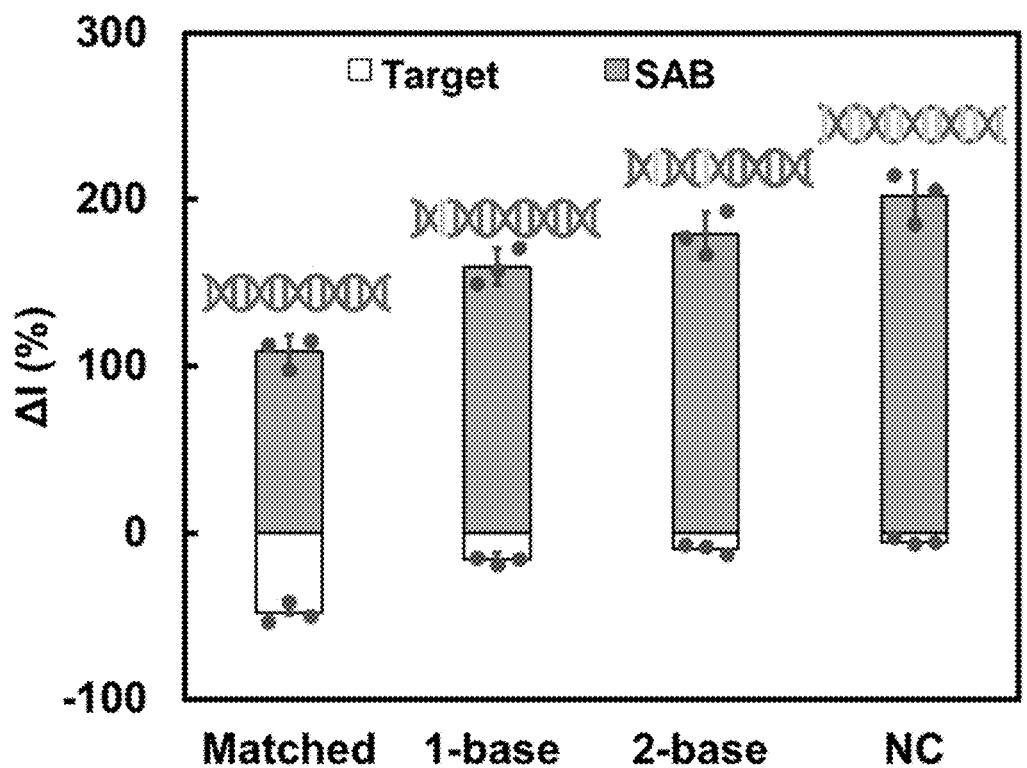

FIG. 10A shows specificity of the differential assay in exemplary embodiments of the disclosure. FIG. 10A shows change in PEC current following hybridization with 1 pM of matched, 1-base mismatched, 2-base mismatched, and NC targets and SAB binding measured in 0.1 M PBS with 0.1 M AA.

Figure 10B:
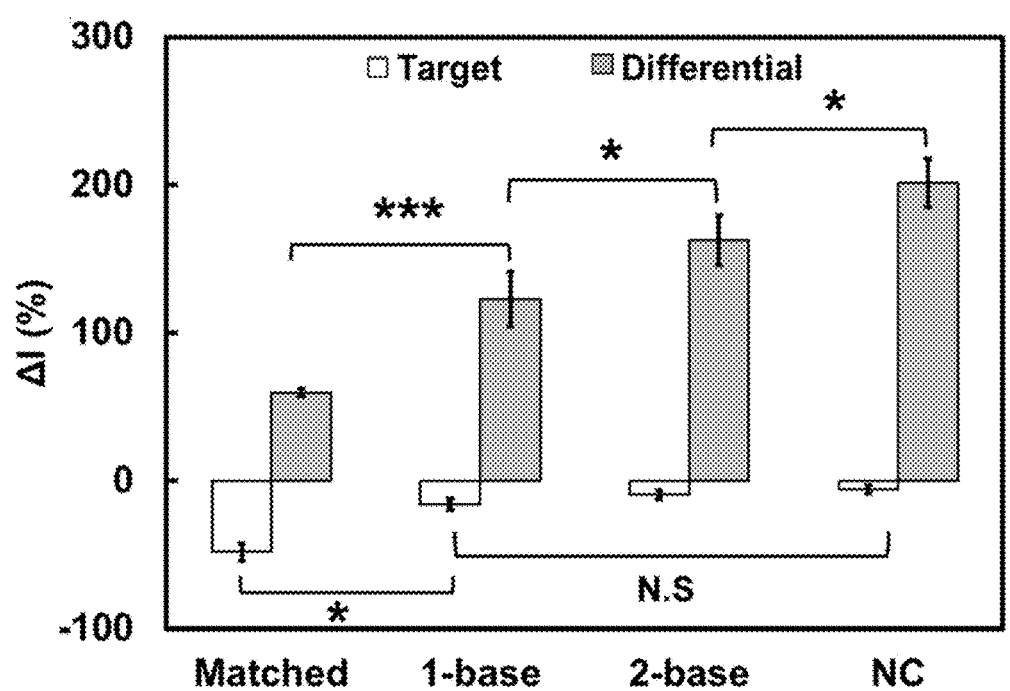

FIG. 10B shows specificity of the differential assay in exemplary embodiments of the disclosure. FIG. 10B shows differential and signal-off responses for the target sequences in FIG. 10A with * and *** representing p<0.05 and p<0.001, respectively.

Figure 11A:
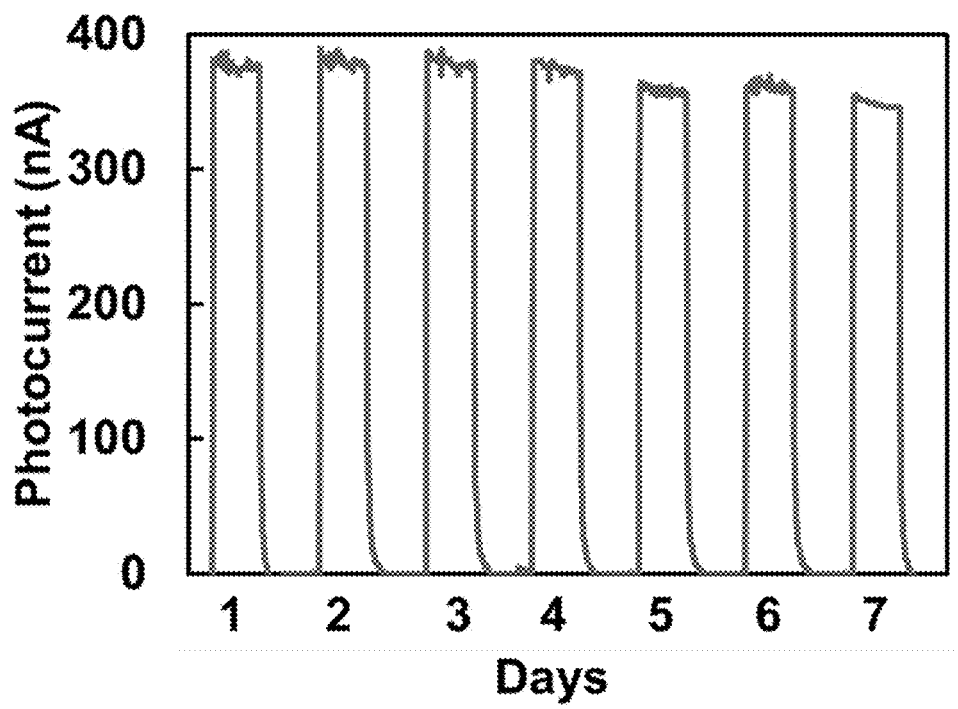

FIG. 11A shows evaluation of the stability of the PEC biosensor in exemplary embodiments of the disclosure. FIG. 11A shows photocurrent measurement following the storage of probe modified electrodes for a period spanning 1-7 days. All photocurrent measurements were performed by applying 0 V vs. Ag/AgCl using 0.1 M ascorbic acid in 0.1 M PBS as electrolyte.

Figure 11B:
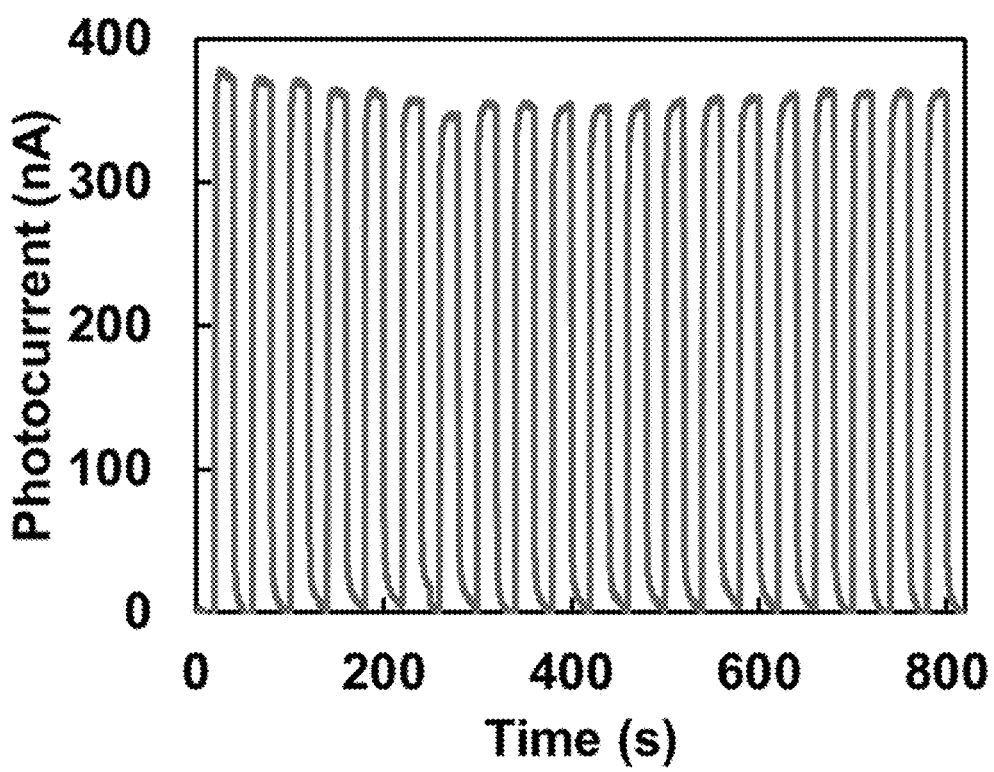

FIG. 11B shows evaluation of the stability of the PEC biosensor in exemplary embodiments of the disclosure. FIG. 11B shows photocurrent measurement for 15 repeated cycles after probe modification. All photocurrent measurements were performed by applying 0 V vs. Ag/AgCl using 0.1 M ascorbic acid in 0.1 M PBS as electrolyte.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art. It is also to be understood that the terminology used herein is for the purpose of describing particular aspects only and is not intended to be limiting.

The term "sample" or "test sample" as used herein refers to any material in which the presence or amount of a target analyte is unknown and can be determined in an assay. The sample may be from any source, for example, any biological (e.g. human or animal samples, including clinical samples), environmental (e.g. water, soil or air) or natural (e.g. plants) source, or from any manufactured or synthetic source (e.g. food or drinks). The sample may be comprised of or is suspected of comprising one or more analytes. The sample may be a "biological sample" comprising cellular and non-cellular material, including, but not limited to, tissue samples, urine, blood, serum, other bodily fluids and/or secretions. In some embodiments, the sample comprises tissue samples, urine, blood, serum, other bodily fluids and/or secretions.

The term "target", "analyte" or "target analyte" as used herein refers to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism and virus, for which one would like to sense or detect. The analyte may be either isolated from a natural source or is synthetic. The analyte may be a single compound or a class of compounds, such as a class of compounds that share structural or functional features. The term analyte also includes combinations (e.g. mixtures) of compounds or agents such as, but not limited, to combinatorial libraries and samples from an organism or a natural environment. In some embodiments, the target is not labeled.

The term "nucleic acid" as used herein refers to a polynucleotide, such as deoxyribonucleic acid (DNA), ribonucleic acid (RNA), modified nucleotides and/or nucleotide derivatives, and may be either double stranded (ds) or single stranded (ss). In some embodiments, modified nucleotides may contain one or more modified bases (e.g. tritiated bases and unusual bases such as inosine), modified backbones (e.g. peptide nucleic acid, PNA) and/or other chemically, enzymatically, or metabolically modified forms.

The term "capture probe" as used herein refers to a molecule (e.g. compound) that recognizes and binds (e.g. hybridizes) to a target analyte and/or a reporter moiety. The capture probe can be a part of a population of capture probes in which each probe has identical or similar physical properties and thus have identical functional activity, for example, in binding to a target analyte or a reporter moiety. The capture probe may comprise a nucleic acid, including aptamer and/or DNAzyme, and/or protein, including enzyme, and/or antibody. In some embodiments, a capture probe comprises a nucleic acid, aptamer, DNAzyme, enzyme, and/or antibody. In some embodiments, the capture probe is immobilized or coupled to a support, for example, a photoelectrode. In some embodiments, the capture probe is functionalized on a photoelectrode. In some embodiments, the capture probe comprises a biopolymer. In some embodiments, the capture probe comprises a nucleic acid having nucleic acid sequence that hybridizes to a complementary or partially complementary sequence.

The term "reporter moiety" as used herein refers to a moiety comprising a molecule (e.g. compound) for reporting the presence of an analyte. For example, the moiety is used for reporting the presence of an analyte recognized by the capture probe as a detectable signal. The reporter moiety may be a molecule modified with a detectable label. The reporter moiety may be a molecule modified with a redox, photoelectrochemical, passivating, semi-conductive and/or conductive species. In some embodiments, the reporter moiety comprises a molecule modified with a detectable label. In some embodiments, the reporter moiety comprises a detectable label and a capture probe binding portion. In some embodiments, the reporter moiety comprises a nucleic acid modified with a detectable label. In some embodiments, the detectable label is a single detectable label.

The term "hybridization" or "hybridize" as used herein refers to the sequence specific non-covalent binding interaction with a complementary, or partially complementary, nucleic acid sequence. Binding by complementarity has the same meaning as hybridizing, referring to the sequence specific non-covalent binding interaction with a complementary, or partially complementary, nucleic acid sequence.

The term "functionalizing" or "functionalized on" as used herein refers to various common approaches for functionalizing a material, which can be classified as mechanical, physical, chemical and biological. Any suitable form of coupling may be utilized (e.g. coating, binding, etc.).

The term "photoelectrode" or "photoactive electrode" as used herein refers to a semiconducting material having a photoactive material such as a photocatalyst. A photoelectrode may be a layer such as a transparent electrode layer disposed on the light incident side or on the viewing (observation) side. A photoelectrode can include a conductive substrate having a photoactive material (e.g. semiconductor coating). The substrate may include glass, polymer, metal or a combination thereof. The polymer may include polyethylene terephthalate (PET), polyethylene naphthalate (PEN) or polyimide (PI). If the substrate of the conductive substrate is made of non-conductive glass or polymers, a conductive material is provided such as, for example, indium tin oxide (ITO), fluorine-doped tin oxide (FTO), antimony-doped tin oxide (ATO), aluminum-doped zinc oxide (AZO), gallium-doped zinc oxide (GZO), indium-doped zinc oxide (IZO) or a combination thereof. In some embodiments, the photoelectrode is a single photoelectrode. In some embodiments, the photoactive material is a single photoactive material.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies. In addition, all ranges given herein include the end of the ranges and also any intermediate range points, whether explicitly stated or not.

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The abbreviation, "e.g." is derived from the Latin exempli gratia and is used herein to indicate a non-limiting example. Thus, the abbreviation "e.g." is synonymous with the term "for example." The word "or" is intended to include "and" unless the context clearly indicates otherwise.

Although methods and materials similar or equivalent to those described herein can be used in the practice or testing of this disclosure, suitable methods and materials are described below.

II. Biosensors and Methods of the Disclosure

The present disclosure discloses a PEC biosensing strategy that uses differential signal generation, combining signals from two separate but correlated binding events on a single biosensor, for improving the limit-of-detection, sensitivity, and specificity of PEC DNA biosensors in biological samples. In this assay, the binding of, for example, unlabeled target DNA is followed by the capture of a signal amplification barcode featuring, for example, a plasmonic nanoparticle. The interaction of the plasmonic barcode with the semiconductive building blocks of the biosensor results in significant signal amplification, and together with differential signal processing enhances the limit-of-detection and sensitivity of the assay by, for example, up to 15 and three times, respectively, compared to the previously-used PEC assays with a single binding event, demonstrating a limit-of-detection of, for example, 3 fM.

The differential biosensor comprises, for example, a $TiO_2$/Au system, using Au nanoparticles (Au NPs) as the sole PEC species. To achieve this, two subsequent and correlated PEC measurements were used in the disclosed embodiments. First, the change in PEC current induced by the binding of an unlabeled target to a capture probe DNA was measured. Second, the additional PEC current change obtained when the unreacted capture probes were bound to a signal amplifying barcode (SAB) generated from AuNP-labeled DNA strands, for signal amplification. The signal changes measured during the two binding events were differentially combined to enhance the limit of detection (LDO) of the system. The use of SAB as an amplification sequence builds on the premise that plasmonic NPs in direct contact or close proximity to semiconducting materials possessing favorable energetics, modulate carrier lifetime, thus, altering the PEC current. Using this differential strategy, the influence of background contributions is effectively suppressed, which in turn, for example, enhanced sensitivity by more than three times and LOD by 14 times compared to an analogues assay that measured a single binding event.

Accordingly, provided herein is a biosensor for detecting a target analyte in a sample comprising:
a) a photoelectrode comprising a conductive substrate and a photoactive material;
b) a population of capture probes functionalized on the photoelectrode wherein the capture probes are capable of binding to the target analyte and a reporter moiety; and
c) the reporter moiety comprising a detectable label and a capture probe binding portion;
wherein exposure of the target analyte to the population of the capture probes of b) results in binding of the target analyte to a fraction of the population of capture probes which results in a decrease in the intensity of detection signal compared to the intensity of detection signal in the absence of exposure of the target analyte,
wherein the binding of the target analyte to a fraction of the population of capture probes of b) results in a population of remaining unbound capture probes, and
wherein subsequent binding of the reporter moiety to the population of remaining unbound capture probes of c) results in an increase in intensity in detection signal that is less than an increase in intensity in detection signal from binding of the reporter moiety to a population of capture probes that has not been exposed to the target analyte.

In some embodiments, the reporter moiety is referred to as a signal amplifying barcode (SAB).

In some embodiments, the capture probe binds to the reporter moiety after detecting the target analyte. In some embodiments, the binding of the reporter moiety to the capture probes displaces the target analyte bound to the capture probes.

In some embodiments, the detectable signal is a change in photoelectrochemical current, voltage or impedance. In some embodiments, the detectable signal is a change in photoelectrochemical current.

In some embodiments, the capture probe regulates distance between the detectable label and the conductive substrate.

In some embodiments, binding the target analyte is configured to provide a decrease in the detectable signal and binding the reporter moiety is configured to provide an increase in the detectable signal. In some embodiments, the different detectable signals are combined to create a single differential signal. In some embodiments, the detectable signal resulting from target binding is subtracted from the detectable signal resulting from reporter moiety binding.

In some embodiments, a decrease in the detectable signal upon target analyte binding is due to steric hindrance.

In some embodiments, the capture probe comprises a biopolymer. In some embodiments, the capture probe comprises a nucleic acid sequence that hybridizes to the target analyte and/or reporter moiety. In some embodiments, the capture probe comprises single-stranded DNA, single-stranded RNA, single-stranded PNA, double-stranded DNA, and/or double-stranded RNA. In some embodiments, the capture probe comprises a functional nucleic acid. In some embodiments, the functional nucleic acid is an aptamer or DNAzyme. In some embodiments, the functional nucleic acid is an RNA-cleaving DNAzyme. In some embodiments, the functional nucleic acid comprises ssDNA, ssRNA and/or ssPNA.

In some embodiments, the capture probe comprises a nucleic acid. In some embodiments, the nucleic acid comprises single-stranded DNA. In some embodiments, the single-stranded DNA is an aptamer or DNAzyme.

In some embodiments, the target analyte comprises a nucleic acid. In some embodiments, the nucleic acid is a microRNA (e.g. 18-25-mer) or short DNA barcode released from DNA machines (e.g. less than 40-mer). In some embodiments, the nucleic acid is an 18-25-mer. In some embodiments, the nucleic acid is a DNA of less than 40 nucleotides. In some embodiments, the target analyte is a DNA barcode. In some embodiments, the DNA barcode is released from DNA machines. In some embodiments, the DNA machines comprise DNAzymes, CRISPR-Cas systems, or strand displacement-based systems. In some embodiments, the target analyte comprises a non-nucleic acid. In some embodiments, the target analyte is a protein. In some embodiments, the target analyte binds to the capture probe at the same portion of the capture probe as the reporter moiety. In some embodiments, the target analyte binds to the capture probe at a portion of the capture probe that overlaps with the portion of the capture probe that binds to the reporter moiety.

In some embodiments, the reporter moiety comprises a nucleic acid.

In some embodiments, hybridization occurs between a fraction of the total capture probe population and the target analytes, leaving behind a population of available unhybridized (unbound) probe strands. In some embodiments, the reporter moiety (e.g. SAB strand) hybridizes with the available (unbound) probe strands.

In some embodiments, the capture probe is smaller than or equal to the target analyte in size. In some embodiments, the capture probe is smaller than or equal to the reporter moiety in size. In some embodiments, the length of the nucleic acid capture probe (e.g. 15-mer) is shorter than the length of the nucleic acid reporter moiety (e.g. 25-mer), with the resulting DNA complex containing both double and single stranded regions.

In some embodiments, the capture probe is larger than the target analyte and/or reporter moiety in size. In some embodiments, the nucleic acid capture probe is longer than the target analyte and/or reporter moiety if only a portion of the target analyte and/or reporter moiety is hybridized to the capture probe. In some embodiments, the nucleic acid capture probe is longer than the target analyte and/or reporter moiety if only a portion of the target analyte and/or reporter moiety is partially hybridized via a toe-hold moiety.

In some embodiments, the biosensor further comprises a surface blocker. In some embodiments, the surface blocker comprises monoethanolamine, mercaptohexanol and/or polyethylene glycol. In some embodiments, the surface blocker prevents nonspecific binding to unbound capture probe.

In some embodiments, the biosensor can detect and/or distinguish nucleic acid targets from a mismatched sequence (e.g. single- or double mismatched base pair). In some embodiments, the mismatched sequence is a single mismatched base pair or a double mismatched base pair.

In some embodiments, the conductive substrate comprises metal, glass, polymer or a combination thereof.

In some embodiments, the conductive substrate comprises non-conductive glass or polymer and a conductive material. In some embodiments, the conductive material comprises indium tin oxide (ITO), fluorine-doped tin oxide (FTO), antimony-doped tin oxide (ATO), aluminum-doped zinc oxide (AZO), gallium-doped zinc oxide (GZO), indium-doped zinc oxide (IZO), or a combination thereof. In some embodiments, the polymer comprises polyethylene terephthalate (PET), polyethylene naphthalate (PEN), polyimide (PI), or a combination thereof. In some embodiments, the conductive substrate comprises non-conductive glass or polymer and a conductive material, wherein the conductive material comprises indium tin oxide (ITO), fluorine-doped tin oxide (FTO), antimony-doped tin oxide (ATO), aluminum-doped zinc oxide (AZO), gallium-doped zinc oxide (GZO), indium-doped zinc oxide (IZO), or a combination thereof, and the polymer comprises polyethylene terephthalate (PET), polyethylene naphthalate (PEN), polyimide (PI), or a combination thereof.

In some embodiments, the conductive substrate comprises indium tin oxide.

In some embodiments, the photoactive material comprises thin films, photoactive particles, nanoparticles, microparticles, nanowires, nanorods, nanostars, nanomaterial, conductor materials, semiconductor materials, metals, metal oxides, carbon-based materials, conductive polymers, photoactive polymers, plasmonic materials, dyes, sulfide, metal chalcogenide, cadmium telluride, or a combination thereof. In some embodiments, the photoactive material comprises photoactive particles, nanomaterial, or a combination thereof. In some embodiments, the photoactive material comprises thin films, nanoparticles, microparticles, nanomaterial, or a combination thereof. In some embodiments, the photoactive material comprises nanoparticles, microparticles, nanowires, nanorods, nanostars, or a combination thereof. In some embodiments, the photoactive material comprises conductor materials and/or semiconductor materials. In some embodiments, the sulfide is cadmium sulfide.

In some embodiments, the photoactive material comprises metal(s), metal oxide(s), semiconductor material(s), carbon-based material(s), conductive polymer(s), photoactive polymer(s), plasmonic material(s), dye(s), or a combination thereof.

In some embodiments, the photoactive material comprises metal oxide(s), sulfide(s), metal chalcogenide, or a combination thereof.

In some embodiments, the metal oxide(s) are selected from the group consisting of Cd, Zn, In, Pb, Mo, W, Sb, Bi, Cu, Hg, Ti, Ag, Mn, Fe, V, Sn, Zr, Sr, Ga, Si, Cr, a perovskite such as $SrTiO_3$ or $CaTiO_3$, and a combination thereof.

In some embodiments, the metal chalcogenide is selected from the group consisting of CdSe, $In_2Se_3$, $WSe_2$, HgS, PbSe, CdTe, and a combination thereof.

In some embodiments, the photoactive material comprises titanium dioxide, zinc oxide, iron oxide, cadmium sulfide, cadmium telluride, or a combination thereof.

In some embodiments, the photoactive material comprises titanium dioxide. In some embodiments, the photoactive material is a single photoactive material. In some embodiments, the photoactive material is titanium dioxide.

In some embodiments, the titanium dioxide has a crystal structure that is at least one of anatase, rutile and brookite.

In some embodiments, the titanium dioxide is $P25-TiO_2$.

In some embodiments, the detectable label comprises a plasmonic nanoparticle, organic dye, light absorbing molecule, semiconductive nanoparticle, a metal, semiconductive quantum dot, organic semiconductor, gold nanoparticle, or a carbon-based nanomaterial. In some embodiments, the detectable label comprises a plasmonic nanoparticle, organic dye, light absorbing molecule, semiconductive nanoparticle, or a carbon-based nanomaterial. In some embodiments, the detectable label comprises a metal, semiconductive quantum dot or organic semiconductor. In some embodiments, the detectable label comprises a gold nanoparticle. In some embodiments, the detectable label is a single detectable label. In some embodiments, the detectable label is a gold nanoparticle.

In some embodiments, the biosensor is used for clinical diagnostic, agricultural diagnostics, agri-food quality control, environmental monitoring, health screening, health monitoring, and/or pharmaceutical development.

Also provided herein is a method of detecting a target analyte in a sample, the method comprising
    a) contacting the sample with the photoelectrode of the biosensor disclosed herein under conditions for binding the target analyte to a fraction of the population of capture probes functionalized on the photoelectrode, wherein the binding of the target analyte to a fraction of the population of capture probes results in a population of remaining unbound capture probes;

b) measuring a detectable signal generated from a);

c) introducing the reporter moiety to the photoelectrode of the biosensor disclosed herein under conditions for binding the reporter moiety to the remaining unbound capture probes; and d) measuring a detectable signal generated from c);

wherein the binding of the target analyte to a fraction of the population of the capture probes in a) results in a decrease in the intensity of detection signal compared to the intensity of detection signal in the absence of any binding of the target analytes to the population of the capture probes;

wherein in c) introducing the reporter moiety to the photoelectrode results in the binding of the reporter moiety to the population of remaining unbound capture probes which results in an increase in intensity in detection signal that is less than an increase in intensity in detection signal from binding of the reporter moiety to a population of capture probes that has not been exposed and not bound to the target analyte; and wherein a decrease in the signal intensity measured in b) from the capture probes binding the target analyte and an increase in the signal intensity measured in d) from the capture probes binding the reporter moiety indicates the presence of the target analyte in the sample.

In some embodiments, the detectable signal measured in the method is a change in photoelectrochemical current. In some embodiments, the detectable signal measured in b) is a change in photochemical current induced by the binding of the target analyte to the fraction of the population of the capture probes, and the detectable signal measured in d) is an additional change in photoelectrochemical current induced by the reporter moiety binding to the remaining unbound capture probes.

In some embodiments, the method further comprises calculating a difference and/or ratio between the detectable signal measured in b) from the capture probes binding the target analyte and measured in d) from the capture probes binding the reporter moiety. In some embodiments, the different detectable signals are combined to create a single differential signal.

In some embodiments, the absolute value of photoelectrochemical current decrease after target binding is subtracted from the absolute value of photoelectrochemical current enhancement after reporter moiety binding.

In some embodiments, detection of a differential signal enables highly distinguishable signal footprints.

In some embodiments, the combination of the signal intensity changes induced from a) and c) increase sensitivity in detecting the target analyte.

In some embodiments, the sample comprises tissue samples, urine, blood, serum, other bodily fluids and/or secretions.

A device, or kit for detecting a target analyte in a sample, comprising the biosensor described herein and/or components for the method described herein, and instructions for use are also provided. In some embodiments, the kit comprises a buffer, a diluent, a carrier, or a combination thereof.

Use of the biosensor, device and/or kit described herein are also provided. In some embodiments, the use comprises clinical diagnostic, agricultural diagnostics, agri-food quality control, environmental monitoring, health screening, health monitoring, and/or pharmaceutical development.

EXAMPLE

The following non-limiting Example is illustrative of the present disclosure:

Example 1: Enhancing the Sensitivity of Photoelectrochemical DNA Biosensing Using Plasmonic DNA Barcodes and Differential Signal Readout Materials and Methods Materials and Reagents Phosphate buffer solution (PBS, 0.1 M, pH 7.4), Potassium ferricyanide(III) ($K_3Fe(CN)_6$), potassium hexacyanoferrate(II) trihydrate ($K_4Fe(CN)_6 \cdot 3H_2O$), L-ascorbic acid (99%), sodium chloride (NaCl), Magnesium chloride ($MgCl_2$), ethanolamine (MEA), chitosan (CHIT, from shrimp, degree of deacetylation of 85%, Mw=200,000), glacial acetic acid, 3,4-dihydroxybenzlaldehyde (DHB), hexaammineruthenium (III) chloride ($Ru(NH_3)Cl_3$), Tris buffer, 4-arm polyethylene glycol (PEG) with molecular weight 5000 (PEG-5K), and tris (2-carboxyethyl) phosphine hydrochloride (TCEP, 98%) were purchased from Sigma-Aldrich. P25-titanium dioxide ($TiO_2$) was obtained from Nippon aerosol Co. Ltd. Acetone and Ethanol were purchased from commercial alcohols (Brampton, ON, Canada). Milli-Q grade (18.2 MΩ-cm) de-ionized (DI) water was used for all solution preparation and washing steps. 100 nm indium tin oxide (ITO) glass slides were purchased from Sigma-Aldrich.

Preparation of Surface-Modified $TiO_2$ Nanoparticles (NPs)

$TiO_2$ NPs were prepared using the protocol reported by Victorious et al.[1] Briefly, 3 $gL^{-1}$ CHIT solution was prepared in 1% acetic acid. A 16 $gL^{-1}$ DHB solution was prepared in DI water. A DHB-modified CHIT solution was prepared by maintaining the mass ratio of 4:1 for DHB:CHIT. This solution was obtained by adding DHB solution to the CHIT solution. Finally, 60 mg of P25-$TiO_2$ was added to 15 ml of the DHB-modified CHIT solution.

$TiO_2$ Substrate Preparation

ITO glass substrates were treated with air plasma for 1 minute. Prior to the plasma treatment, substrates were masked using vinyl tape for separating contact area and electrode area. This was also used to ensure the uniformity of the geometric surface area of the electrode. $TiO_2$ films were prepared by placing 10 μL of the surface modified $TiO_2$ solution onto the ITO substrate surface and subsequently baking at 95° C. for 5 minutes. This last step was repeated 3 times. Finally, the electrodes were washed and then air dried before using.

Gold (Au) NP Synthesis

Citrate capped Au NPs were synthesized according to the protocol reported by Grabar et al.[2] Briefly, aqueous gold chloride ($HAuCl_4$) solution (1 mM) was mixed with 38.8 mM trisodium citrate solution with a volume ratio of 10:1. This solution was heated under vigorous stirring for 10 minutes, and then the stirring was continued for an additional 15 minutes without applying heat. The diameter of the prepared Au NPs was approximately 12 nm.

AuNP-DNA Conjugation

DNA conjugation with Au NPs was accomplished by using the protocol provided by Zhang et al.[3] Briefly, 1 ml of 1.2 nM AuNPs was resuspended in 10 mM PBS (pH 7.0).

A 100 µM solution of thiolated DNA was reduced by mixing 1 µl of 10 mM TCEP with 35 µl of the DNA. DNA was incubated in this solution for 30 minutes. Reduced thiolated DNA was added to the AuNP solution and this was incubated for 16 hours at room temperature. After the incubation step, 10 mM PBS and 2 M NaCl solutions were added to the DNA mixture as slowly as possible to make the final salt concentration as 0.1 M NaCl. This solution was incubated for 40 hours at room temperature. This solution was occasionally shaken in order to avoid aggregation. Finally, the solution was washed three times and resuspended in 10 mM PBS with 0.1 M NaCl (pH 7.0) and stored at 4° C.

Photoelectrochemical (PEC) Characterization

PEC measurements were conducted in a three-electrode electrochemical cell using a Zahner CIMPS system. Optical excitation was achieved using a 405 nm LED from the tunable optical light source (TLS03). A Pt wire was used as the counter electrode, Ag/AgCl as the reference electrode, and the deposited $TiO_2$ photoelectrode as the working electrode. All PEC measurements were performed at an applied potential of 0 V (vs. Ag/AgCl). The electrolyte used for all PEC measurements was 0.1 M PBS with 0.1 M ascorbic acid (AA), where AA served as hole scavenger. Period of light excitation was 40 s with a 50% duty cycle (illumination time 20 s). Baseline correction was performed on the measured photocurrents prior to plotting to the data for the figures.

Electrochemical Characterization

Electrochemical impedance spectroscopy (EIS) measurements were performed on the Zahner potentiostat under the open circuit potential. The measurements were performed within the frequency range of 100 kHz to 0.1 Hz in a solution containing 2 mM $[Fe(CN)_6]^{3-/4-}$, 0.1 M PBS, and 0.1 M KCl. Cyclic voltammetry was performed by using 10 mM PBS as electrolyte and 50 mV/s scan rate.

Probe Density Measurement

The probe density of the DNA modified $TiO_2$ electrodes was measured by following the protocol described by Steel et al.[4] In short, chronocoulometry was performed sequentially in 10 mM Tris-buffer and in 100 µM hexaammineruthenium (III) chloride in 10 mM Tris-buffer, on the DNA modified photoelectrodes. From the two graphs, the difference between y-axis intercepts were measured to determine the charge (Q) of the redox marker (Ruthenium ion in this case). From the charge, surface density of the redox marker is calculated using the following formula:

$$Q = nFA\Gamma_0$$

Where, n indicates the number of electrons per molecule for a redox reaction, F is the faraday constant, A is the area of the surface, and $\Gamma_0$ is the density of adsorbed ruthenium ion. Redox marker density can be converted to DNA probe coverage using the following formula:

$$\Gamma_{DNA} = \Gamma_0 \left(\frac{z}{m}\right) N_A$$

Where, FDNA is the density of probe, m is the number of bases in probe DNA, z is the charge of the redox molecule, and $N_A$ is the Avogadro's number.

DNA Hybridization Experiment

Electrodes were modified with probe DNA by drop depositing 35 µl of 1 µM single stranded probe DNA and incubated for 3 hours at room temperature. Afterwards, a 1 mM MEA solution was deposited as a surface blocker with an incubation time of 50 minutes. A 20 µl solution of unlabeled target DNA with different concentrations was drop deposited on the electrode and incubated for one hour at room temperature. Finally, a 100 pM solution of the AuNP-conjugated DNA (signal amplification barcode (SAB)) was deposited on the electrode and incubated for another 40 minutes at room temperature. After each step, electrodes were rinsed in a wash solution (25 mM PBS, 25 mM NaCl). Percentage change of the photocurrent was calculated in two steps. After target deposition, the measured percentage decrease in signal is:

$$\Delta I_{target} = I_{target} - I_{block}$$

$$\% \Delta I_{target} = (\Delta I_{target} \times 100)/I_{block}$$

'% $\Delta I_{target}$' indicates the percentage change in photocurrent following hybridization of the unlabeled target with immobilized probe, while '$I_{block}$' and '$I_{target}$' represent the signals obtained following MEA incubation and target hybridization, respectively. Similarly, percentage increase after SAB hybridization is calculated as follows:

$$\Delta I_{SAB} = I_{SAB} - I_{target}$$

$$\% \Delta I_{SAB} = (\Delta I_{SAB} \times 100)/I_{target}$$

Here, '% $\Delta I_{SAB}$' indicates the percentage change in photocurrent upon SAB binding by available probe sites following target hybridization. '$I_{SAB}$' represents the signal obtained following the anchoring of SABs at the photoelectrode surface.

The signal for the developed bioassay (% $\Delta I_{diff}$) is the algebraic sum of both percentage changes calculated above and is computed according to the following equation:

$$\% \Delta I_{diff} = \% \Delta I_{target} + \% \Delta I_{SAB}$$

The DNA sequences used in this work are as follows:

```
Probe DNA:
                                    (SEQ ID NO: 1)
5'-NH2-AGG GAG ATC GTA AGC-3'

Complementary target:
                                    (SEQ ID NO: 2)
5'-TTT TTT TTT TGC TTA CGA TCT CCC T-3'

Non-complementary (NC) target:
                                    (SEQ ID NO: 3)
5'-TTT TTT TTT TTT TTT TTT TTT TTT T-3'

DNA for Au NP conjugation:
                                    (SEQ ID NO: 4)
5'-SH-TTT TTT TTT TGC TTA CGA TCT CCC T-3'

1-base mismatch:
                                    (SEQ ID NO: 5)
5'-TTT TTT TTT TGC ATA CGA TCT CCC T-3'

2-base mismatch:
                                    (SEQ ID NO: 6)
5'-TTT TTT TTT TGC ATA CGA TGT CCC T-3'
```

Sensitivity and Limit-of-Detection Calculations

In order to determine the limit-of-detection (LOD) of the assay, the photocurrent change (% $\Delta I_{diff}$) versus the log of target concentration was plotted in the linear range (1 fM-100 pM) for both steps of hybridization. These changes are algebraically added to obtain the differential signal. The linear equation for the regression line is % $\Delta I_{diff} = -49 \log_{10} C + 173$ with a correlation coefficient of 97.97% when the target is in the buffer and % $\Delta I_{diff} = -25 \log_{10} C + 106$ with a correlation coefficient of 99.84% when the target is in diluted urine. The correlation coefficient for both cases is written in FIG. 3B. The limit-of-blank (LOB) was calculated:

$$LOB = \mu_B - 1.645 * \sigma_B$$

Here, '$\mu_B$' is the mean and '$\sigma_B$' is the standard deviation of the background signal, i.e. the signal obtained upon incubation of the photoelectrodes with non-complementary target DNA. The LOD was calculated by determining the concentration where the '% $\Delta I_{diff}$' value of the regression line becomes equal to the LOB. This was done using the following equation:

$$LOD = 10^{\frac{LOB-x}{m}}$$

Here, x' is the x-intercept of the regression line while 'm' denotes the sensitivity of detection and was obtained from the slope of the regression line of the LOD curve.

Similarly, for the signal-off assay, the photocurrent change (% $\Delta I_{target}$) versus the log of target concentration in the linear range (1 fM-100 pM) was plotted following target hybridization alone. The linear equation for the regression line obtained for this data set is % $\Delta I_{target}$=−14 $\log_{10}$C−3 with a correlation coefficient of 98.83% when the target is in the buffer and % $\Delta I_{target}$=−8 $\log_{10}$C−4 with a correlation coefficient of 99.13% when the target is in diluted urine. The LOD was calculated by determining the concentration where the % $\Delta I_{target}$ value of the regression line becomes equal to the LOB. The LOB and LOD of the signal-off assay were then calculated as per the aforementioned protocol.

Urine Sample Analysis

Urine samples were collected from a healthy patient cohort. The urine was diluted 10 times and the target DNA was spiked into the diluted urine. All experiments were performed using the methods in the previous section, except for the shortened, 40-minute, hybridization time.

Plasma Sample Analysis

Human plasma was donated by the Canadian Plasma Resources (Saskatoon, SK, Canada). Target DNA (1 pM) was spiked into the 5 times diluted plasma samples. All experiments were performed similarly to the Urine sample analysis, except 1 mM PEG-5K was used as the surface blocker instead of 1 mM MEA.

Results and Discussion

The differential PEC biosensor was created by combining two sequential but correlated binding events on a single photoelectrode. A porous network of $TiO_2$ NPs was deposited on ITO substrates to create the photoelectrode, yielding the initial photocurrent profile (FIG. 1A, see panel (i)). These photoelectrodes were then bio-functionalized with 15-nucleotide long single stranded DNA (ss-DNA) probes and subsequently blocked with monoethanolamine (MEA) to prevent nonspecific adsorption. The immobilization of probe DNA on the photoelectrode surface was verified using chronocoulometry and the probe coverage was measured as $5 \times 10^{11}$ molecules/$cm^2$ (FIG. 2).

Figure 1A:
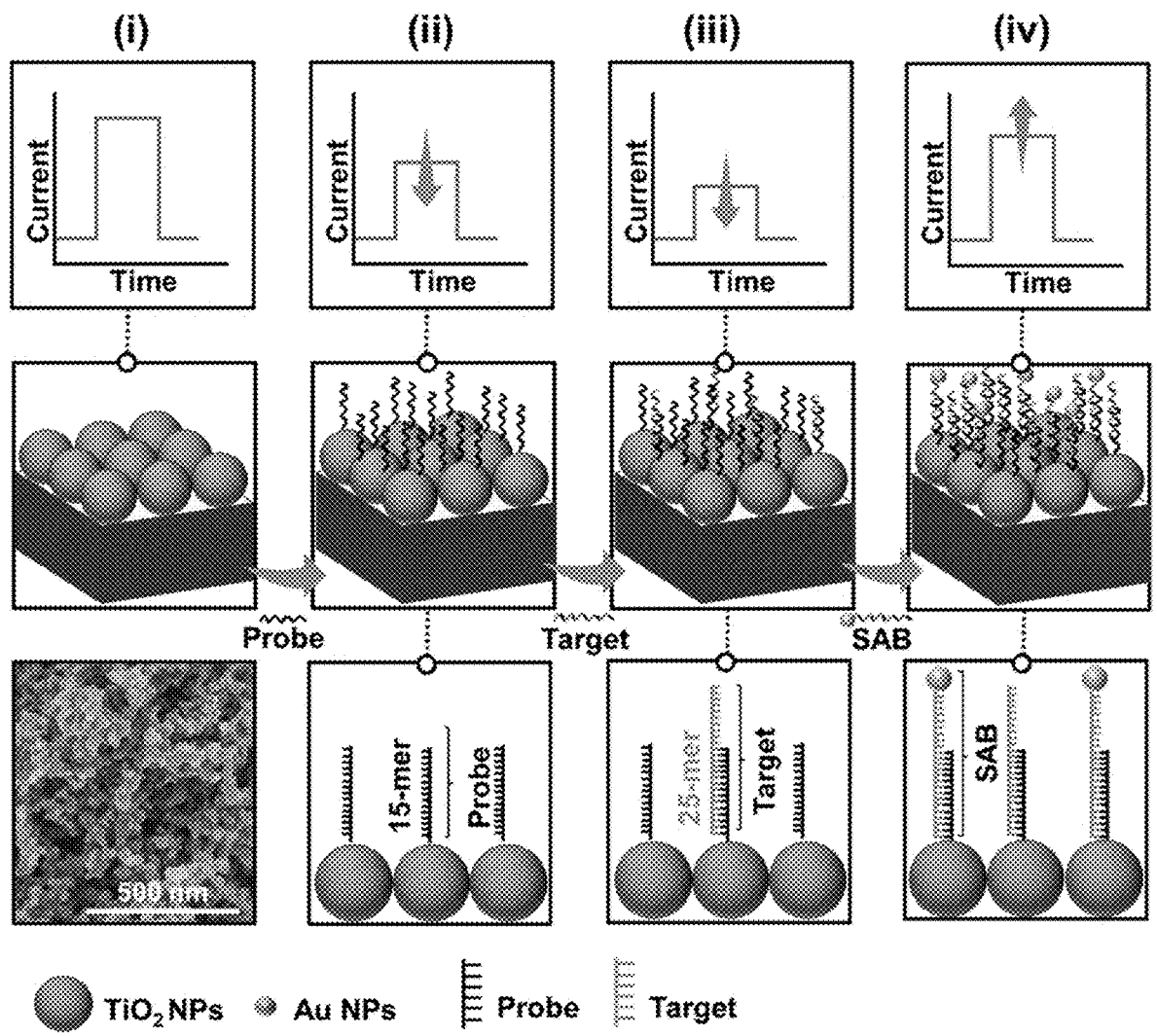
Figure 1B:
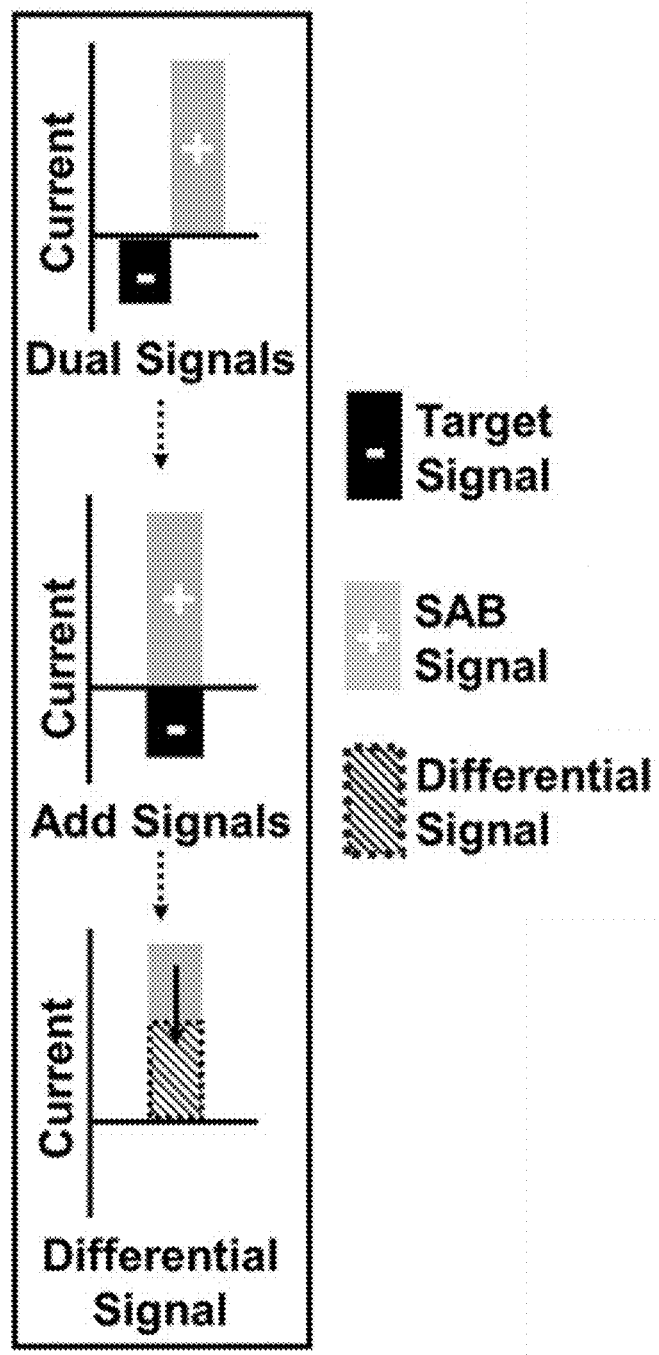
Figure 2:
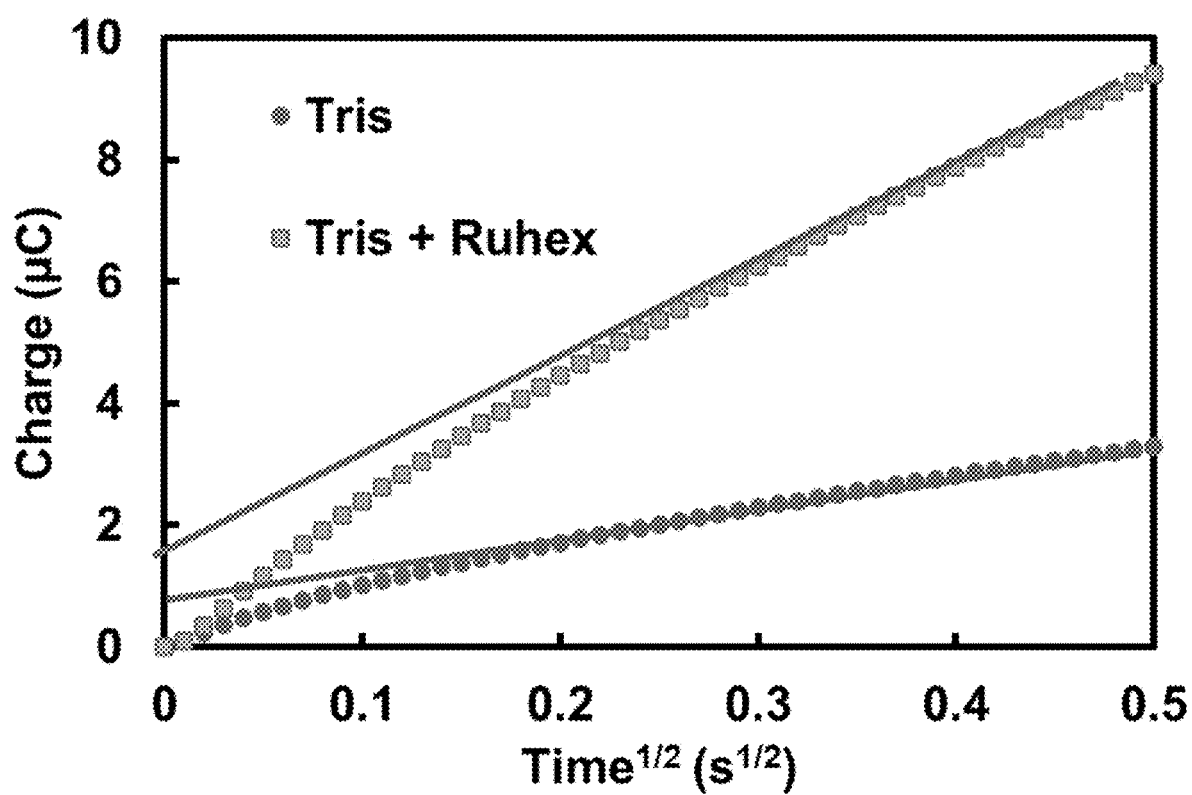

A resulting decrease in photocurrent was anticipated following bio-functionalization due to the induction of steric hindrance between the photoelectrode and the species in the electrolyte (FIG. 1A, see panel (ii)). Upon incubation with 25-mer complementary DNA targets (unlabeled), hybridization occurs between a fraction of the total probe population and the targets, leaving behind a population of available unhybridized probe strands. A further decrease in photocurrent is expected due to steric hindrance (FIG. 1A, see panel (iii)). The SAB strand is then hybridized with the available probe strands. The length of the ssDNA probe (15-mer) is shorter than the length of the SAB strand (25-mer), with the resulting DNA complex containing both double and single stranded regions. It has been previously demonstrated that the Au NPs on the SAB have a high probability of coming into direct contact with $TiO_2$ NPs owing to the dynamic motion of the DNA complex used in this work.[5] Direct contact between Au and $TiO_2$ NPs facilitates charge transfer between the two particles, thereby enhancing the anodic photocurrent (FIG. 1A, see panel (iv)). The DNA sensing approach, involving two hybridization steps, presents at least two benefits: 1) the target DNA strand does not need to be labeled prior to introduction on the chip, and 2) the combination of the signal changes induced from the two hybridization steps is expected to increase the assay sensitivity (FIG. 1B). It should be noted that this two-hybridization approach makes it possible for the SAB binding to result in the displacement (completely or partially) of the target strands. Partial hybridization of the SAB with the existing target-hybridized probes becomes more probable at longer nucleic acid strands. Under the conditions used here, the use of a 15-mer DNA probe, a 25-mer DNA target, a 25-mer SAB strand with the same sequence as the target strand, and a room temperature hybridization step, less than 10% of target strands is expected to be removed by the SAB strand, thus not making competitive strand replacement a significant contributor to the assay performance. As a result of the assay design, it is expected to be well-suited for detecting short nucleic acid targets such as microRNA (18-25 mer) or short DNA barcodes released from DNA machines. MicroRNAs have been identified as clinically important diagnostic biomarkers for various diseases including cancer, cardiovascular conditions, and infectious diseases.

Figure 3A:
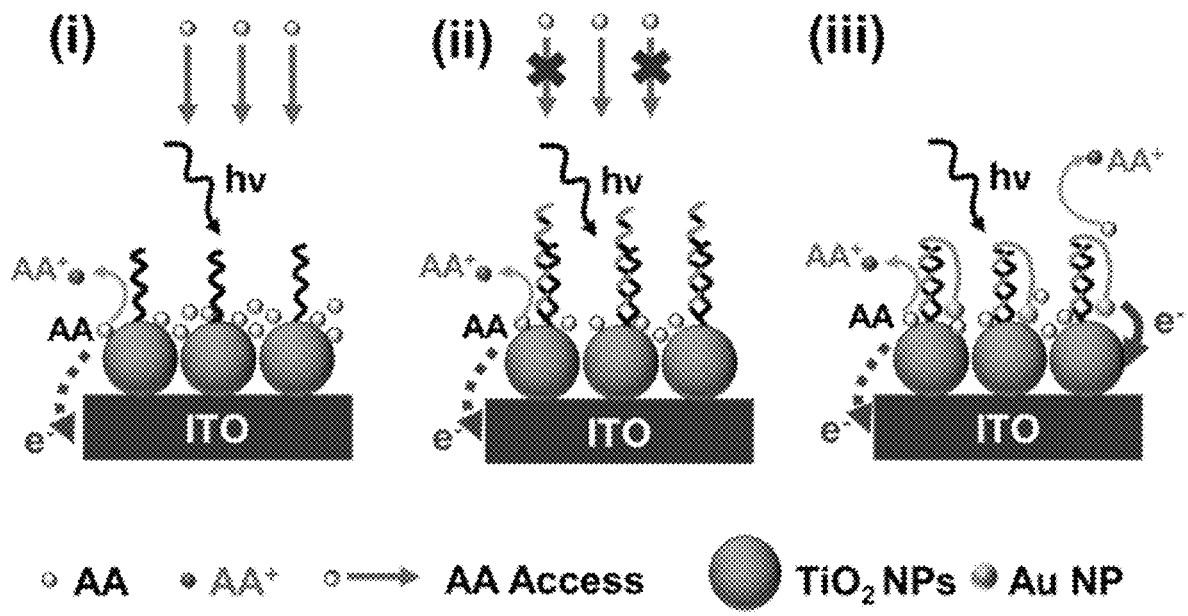
Figure 3B:
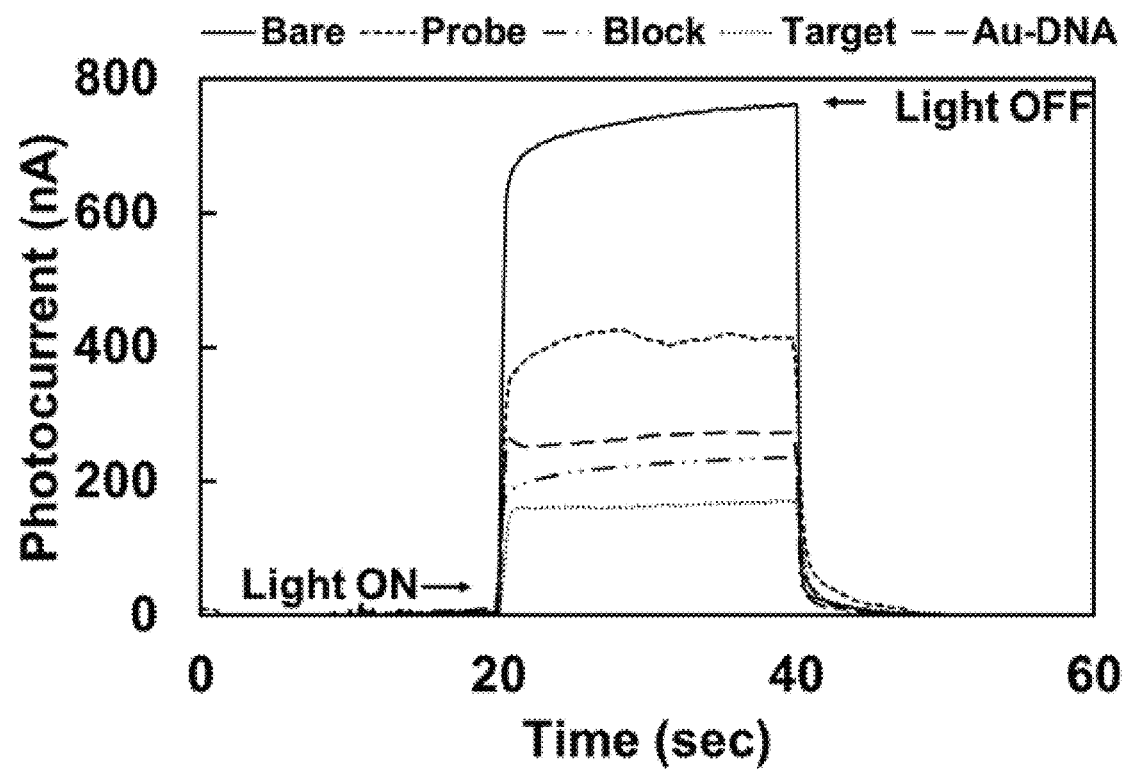
Figure 3C:
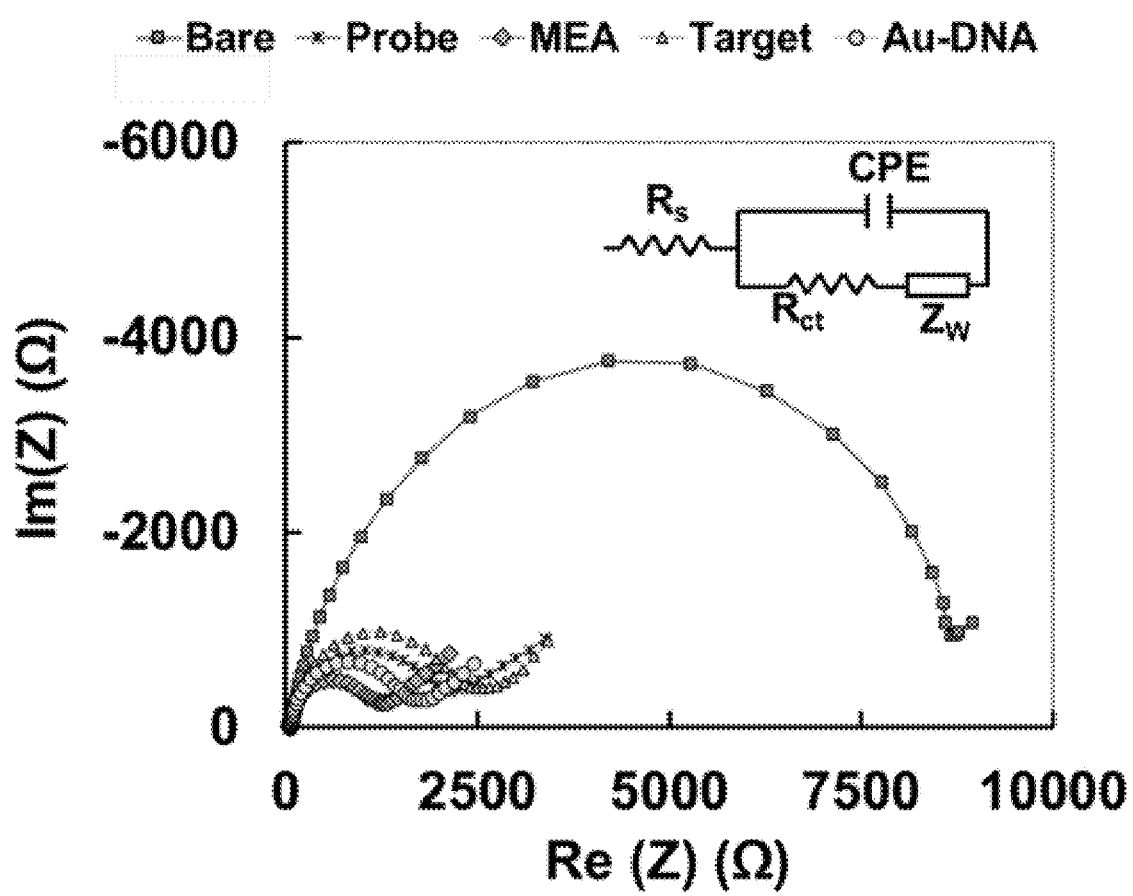

The differential sensor design was verified by measuring the photocurrent and charge transfer resistance in each step of the sensor development process (FIG. 3A, FIG. 3B, and FIG. 3C). For the photocurrent measurements, an LED light source was used with an excitation wavelength of 405 nm and an intensity of 160 W/$m^2$. Ascorbic acid (AA) was used as the hole scavenger to generate anodic current upon optically exciting the electrode (FIG. 3A). A 45% photocurrent decrease was observed after probe deposition due to the steric hindrance of AA caused by the single stranded capture probe (FIG. 3B). Subsequently, MEA was used to block the unbound sites of the working electrode which further decreased the photocurrent by 35% as MEA impedes the access of AA to the surface of $TiO_2$ nanoparticles. Following this, target DNA was introduced on the surface and a 45% photocurrent reduction was observed. As target DNA hybridizes with the capture probe on the photoelectrode, it further hinders the access of AA (FIG. 3A). Finally, a 105% enhancement in photocurrent was observed upon the introduction of the SAB to the substrate (FIG. 3B). Enhancement of photocurrent under UV excitation has been reported in similar systems due to Fermi level equilibration as optically-excited electrons from the conduction band of the semiconductor move to the Au NPs, thereby reducing the carrier recombination rate. Optical excitation at 405 nm can also generate hot electron and hot holes via d-sp transition in Au NPs. It is possible that these hot holes directly oxidize AA, while the hot electrons are transferred to $TiO_2$ NPs, thereby increasing the photocurrent (FIG. 3A).

Figure 4:
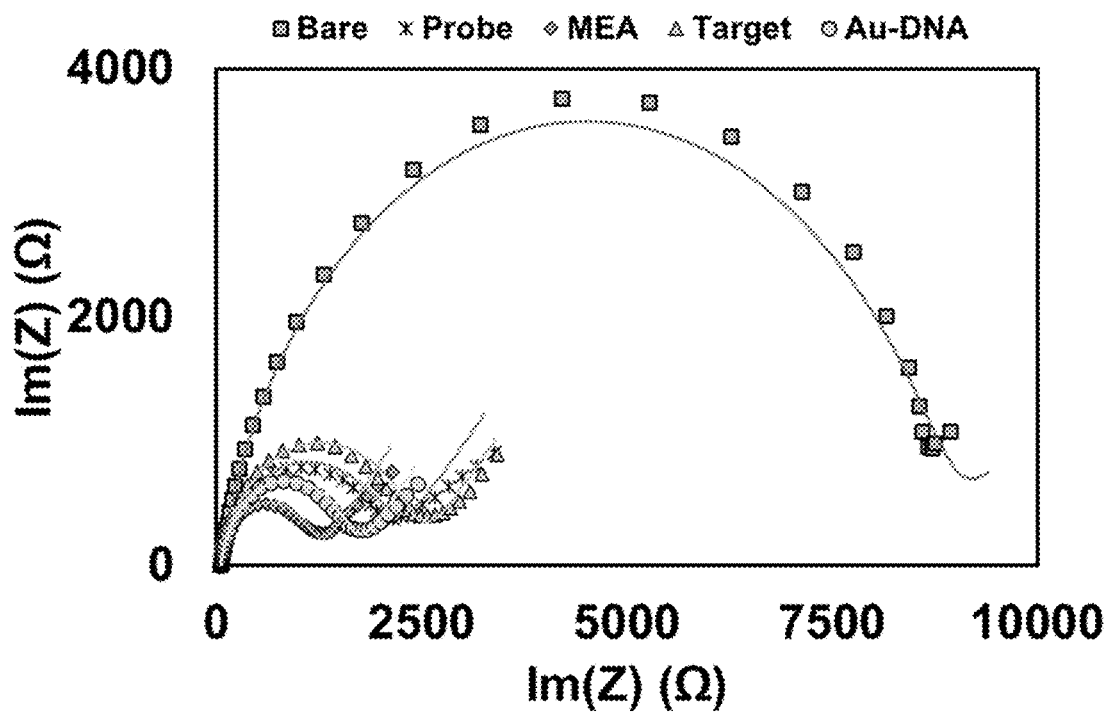
FIG. 4 shows EIS measured at different fabrication steps of the differential PEC biosensor in an exemplary embodiment of the disclosure. The symbols indicate the raw data points, whereas the solid line indicates the fit with the circuit model.
Figure 5:
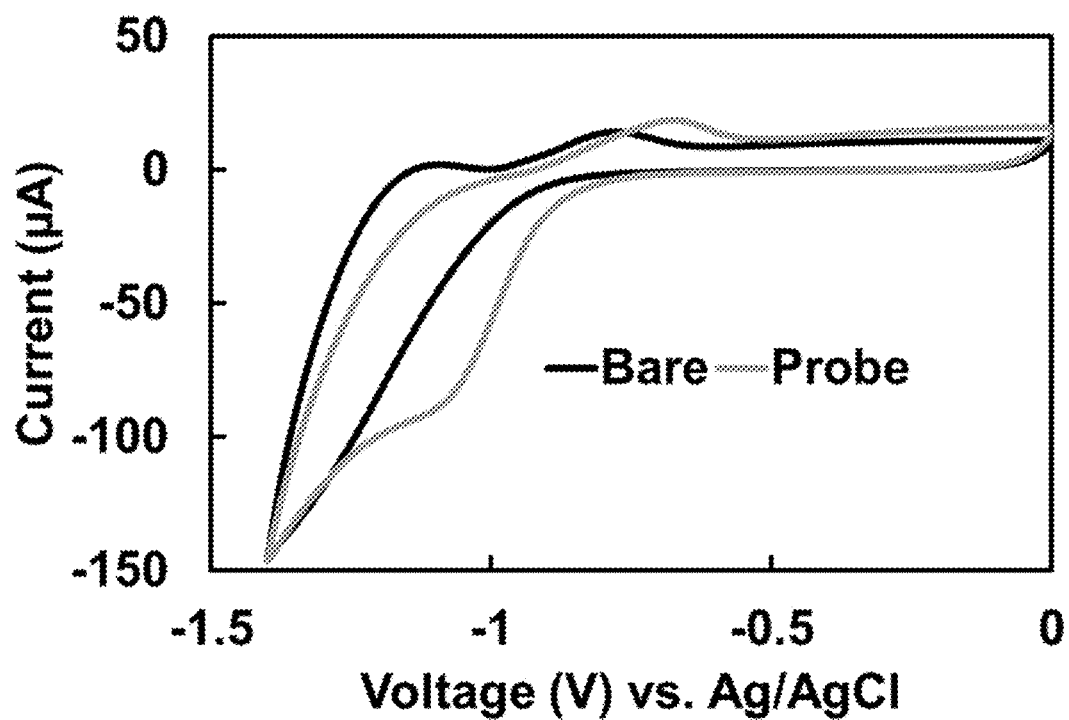
FIG. 5 shows cyclic voltammetry scan for $TiO_2$ electrodes before and after modification with ssDNA using 10 mM PBS as electrolyte and 50 mV/s scan rate in an exemplary embodiment of the disclosure.

Electrochemical impedance spectroscopy (EIS) at open circuit potential was also used to characterize the stepwise fabrication process of the proposed assay design (FIG. 3C). The charge transfer resistance ($R_{ct}$) of the photoelectrode decreased by 78% after DNA probe attachment (Table 1 and FIG. 4). This is contrary to the usual observation found in the literature where probe immobilization increases $R_{ct}$. A study reported by Imani et al. showed that the addition of ssDNA on dopamine modified $TiO_2$ NPs results in a higher electron transfer rate due to the quantum mechanical tunneling effect by bridging the molecular medium between the donor and the acceptor sites of ssDNA and $TiO_2$ NPs, respectively.[6] Therefore, the observed reduction in $R_{ct}$ in this work can also occur due to the amine-modified ssDNA covalently bonding with the aldehyde groups on the 3,4-dihydroxybenzlaldehyde (DHBA) linker on the $TiO_2$ NP surface having the same linker chemistry as dopamine, thereby enhancing the probability of quantum tunneling. DNA functionalization reduces carrier trapping sites by passivating the semiconductor ($TiO_2$) surface, thereby reducing charge recombination.[7] In order to further validate this finding, cyclic voltammetry (CV) was performed in 0.1 M phosphate buffer (PBS) to show changes in charge transfer kinetics (FIG. 5). This study showed that the amount of stored charges in the photoelectrodes were increased from 0.59 mC to 0.72 mC after DNA functionalization, indicating longer lived excitons. Similarly, the addition of MEA as a surface blocker further decreased the charge transfer resistance by 43%. Upon the hybridization of target DNA, the $R_{ct}$ increased by 110%, which is attributed to increased steric hindrance between the redox species in the solution and the surface of the photoelectrode. Introduction of the SAB resulted in a 33% decrease in $R_{ct}$, which is attributed to improved charge transfer kinetics due to the addition of Au NPs into the electrode film.

To assess the ability of the differential PEC biosensor in analyzing DNA targets, this study analyzed unlabeled DNA targets within a concentration range of 1 fM to 100 pM. As expected, when a solution containing target DNA was introduced to the device, the electrodes showed a PEC current that monotonically decreased with increasing target concentration (FIG. 6A). As the concentration of target DNA in the first hybridization step decreases, there is a larger population of residual unhybridized probes, allowing more SAB strands to bind to the photoelectrode yielding a signal increase. As expected, this signal increase is larger at lower target DNA concentrations (FIG. 6A; FIG. 6B, see panel (i)).

The differential PEC sensing strategy is then developed by combining the photocurrent change after target and SAB binding steps. More specifically, the absolute value of photocurrent decrease after target hybridization was subtracted from the absolute value of photocurrent enhancement after SAB binding. The differential signal for each concentration was plotted to generate a calibration curve (FIG. 6B). A linear fit to the calibration curve yields a sensitivity of 49%/$log_{10}$ M and LOD of 3 fM in buffer. The reverse signal-to-concentration effect observed herein, where the largest signals are obtained at the lowest concentrations, allows high signal-to-noise ratios to be obtained at low concentrations that are often needed for clinical analysis, a feature that is not possible with traditional sandwich assays. This increase in signal at lower concentrations comes with the inherent drawback of differential signal processing: the experimental errors obtained from each measurement accumulate in the differential signal, leading to a loss of precision at all concentrations. Additionally, the use of two hybridization steps increases the overall assay time; however, experiments demonstrate that it is possible to reduce the duration of each hybridization step while yielding sufficiently strong signal response for 1 pM DNA target (FIG. 7).

In order to assess the applicability of the differential biosensor in analyzing DNA targets in complex biological matrices, target DNA at various concentrations was spiked into healthy patient urine (FIG. 6C and FIG. 6D). The differential assay yielded a sensitivity of 25%/$log_{10}$ M and LOD of 5 fM in urine. Both LOD and sensitivity deteriorate moderately in urine compared to buffer (less than a factor of two). This can be attributed to the biofouling of the photo electrode caused by the biological components present in urine.

Adding the signal amplification step using the SAB significantly enhances the LOD of the system in both buffer (from 11 fM to 3 fM) and urine (from 73 fM to 5 fM) compared to using a single target binding step (FIG. 8A and FIG. 8B). The large enhancement in LOD (~15 times) observed in urine indicates that the differential signaling strategy is particularly important for compensating for the performance loss that is observed in complex biological samples. In addition to LOD, the differential strategy enhanced the assay sensitivity by about three times compared to the single binding assay for both buffer and urine samples. The bioassay was further challenged by spiking 1 pM target DNA into human blood plasma (FIG. 9). It should be noted that the bioassay utilized polyethylene glycol (PEG), in place of MEA, to reduce non-specific adsorption at the biosensor surface. The photocurrent changes observed after incubating the sensor with the target and SAB strands were similar to when human urine was used, indicating the potential use of this assay for biomarker detection in blood plasma.

To assess the specificity of the nucleic acid biosensor and its ability in distinguishing between fully-matched and mismatched targets presenting point mutations, detection was carried out for targets with sequences having 1-base, 2-base and 3-base mismatches with the original sequences. The photocurrent changes obtained following each hybridization stage (after target and SAB binding) were then evaluated against those obtained for a perfectly complementary and a fully mismatched sequence tested in the same manner (FIG. 10A and FIG. 10B).

Following target binding, the current deceased by 48%±6%, 16%±4%, 14%±9%, and 6%±3% for matched, 1-base mismatched, 2-base mismatched, and non-complementary (NC) sequences, respectively (FIG. 10A). This trend is largely attributed to the varying hybridization efficiency in each scenario, with fewer base mismatches resulting in more efficient target binding. The matched, 1-base mismatched, 2-base mismatched, and NC sequences exhibited a 109%±6%, 160%±9%, 179%±8%, and 202%±4% increase in signal magnitude respectively, following SAB binding (FIG. 10A). In the case of the mismatched sequences, albeit inefficient, a fraction of the target sequences binds to available probe sites, still decreasing the available binding sites for SAB binding, which in turn reduces the SAB-induced signal enhancement. The differential signal enables highly distinguishable signal footprints to be realized for the different sequences with 60%, 123%, 163%, and 201% signal changes measured for matched, 1-base mismatched, 2-base mismatched, and NC sequences (FIG. 10B). A statistical t-test was performed to assess the ability of the assays using one or two binding steps in distinguishing between different degrees of probe/target complementarity. Using differential signaling, matched, 1-base mismatched, 2-base mismatched, and NC sequences were able to be distinguished (FIG. 10B). On the contrary, the single target binding event can only distinguish matched from the 1-base mismatched sequence. The differential approach achieves a superior mismatch specificity with a high confidence level ($p<0.05$ for all scenarios) as compared to its signal-off analogue.

The static and dynamic stability of the differential PEC biosensor was further assessed. PEC measurements of the electrodes stored under static conditions over a 7-day period following probe deposition (FIG. 11A) revealed a small decrease in biosensor photocurrent (8% decrease from day 1 to day 7). Furthermore, the stability of the photoelectrodes under dynamic conditions, multiple light excitation and potential application, was assessed for 15 measurement cycles within a period of 800 s (FIG. 11B), indicating stable photocurrents with a relative standard deviation of 6%.

CONCLUSION

A differential PEC assay using two subsequent and correlated hybridization events, first with an unlabeled target and then with a single amplification barcode tapping into the interaction of plasmatic and semiconductive nanoparticles, to detect unlabeled target DNA in both buffer and urine is described herein. The differential strategy exhibited a LOD of 3 fM in buffer and 5 fM in diluted urine, demonstrating significant improvement over a conventional signal-off strategy that used a single binding event (11 fM in buffer and 72 fM in urine, respectively). In addition to LOD, this assay enhanced the analytical sensitivity by a factor of three compared to an analogous assay that did not use differential signaling. The differential assay also demonstrated the ability to distinguish between sequences that were matched or contained 1- or 2-base mismatches with the detection probe, which was not possible using the non-differential approach. This disclosure offers a strategy for enhancing the limit-of-detection, sensitivity, and specificity of PEC biosensors, performance metrics that are key to the use of PEC biosensors in, for example, clinical decision making.

The biosensor disclosed herein, in terms of target length (25-mer) and concentration range (1 fM-100 pM), is well-suited for the analysis of short nucleic acid strands such as microRNA or DNA barcodes released from DNA machines such as DNAzymes, CRISPR-Cas systems, and strand displacement-based systems.

While the present disclosure has been described with reference to examples, it is to be understood that the scope of the claims should not be limited by the embodiments set forth in the Example, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Tables

TABLE 1

Values of the charge transfer resistance ($R_{ct}$), constant phase element (CPE) and n, indicating the constant phase (−90*n) of the CPE for each step of the construction of the differential biosensor extracted from FIG. 2.

|        | $R_{ct}$ (kΩ) | CPE (μF) | n    |
|--------|---------------|----------|------|
| Bare   | 8.8           | 8        | 0.9  |
| Probe  | 1.96          | 4.6      | 0.85 |
| MEA    | 1.12          | 5.43     | 0.91 |
| Target | 2.36          | 4.07     | 0.87 |
| SAB    | 1.58          | 5.54     | 0.9  |

REFERENCES

[1] A. Victorious, A. Clifford, S. Saha, I. Zhitomirsky, L. Soleymani, J. Phys. Chem. C 2019, 123, 16186-16193.
[2] K. C. Grabar, R. G. Freeman, M. B. Hommer, M. J. Natan, Anal. Chem. 1995, 67, 735-743.
[3] J. Zhang, S. Song, L. Wang, D. Pan, C. Fan, Nat. Protoc. 2007, 2, 2888-2895.
[4] Steel, A. B., Herne, T. M. and Tarlov, M. J., *Anal Chem.* 1998, 70(22), 4670-4677.
[5] S. Saha, A. Victorious, R. Pandey, A. Clifford, I. Zhitomirsky, L. Soleymani, ACS Appl. Mater. Interfaces 2020, 12, 36895-36905.
[6] R. Imani, M. Pazoki, A. Tiwari, G. Boschloo, A. P. F. Turner, V. Kralj-Iglič, A. Iglič, Nanoscale 2015, 7, 10438-10448.
[7] Ö. Ateş Sönmezoğlu, S. Akin, B. Terzi, S. Mutlu, S. Sönmezoğlu, Adv. Funct. Mater. 2016, 26, 8776-8783.

The invention claimed is:

1. A biosensor for detecting a target analyte in a sample comprising: a) a photoelectrode comprising a conductive substrate and a photoactive material; b) a population of capture probes functionalized on the photoelectrode, wherein the capture probes are configured to bind to the target analyte and a reporter moiety; and c) the reporter moiety comprising a detectable label and a capture probe binding portion; wherein exposure of the target analyte to the population of the capture probes of b) is configured to result in binding of the target analyte to a fraction of the population of capture probes, which thereby results in a decrease in the intensity of detection signal compared to the intensity of detection signal in the absence of exposure of the target analyte, and wherein the binding of the target analyte to a fraction of the population of capture probes of b) is configured to result in a population of remaining unbound capture probes, and wherein subsequent binding of the reporter moiety to the population of remaining unbound capture probes of c) is configured to result in an increase in intensity of detection signal that is less than an increase in intensity in detection signal from binding of the reporter moiety to a population of capture probes that has not been exposed to the target analyte.

2. The biosensor of claim 1, wherein the detectable signal is a change in photoelectrochemical current, voltage or impedance.

3. The biosensor of claim 1, wherein the capture probe regulates distance between the detectable label and the conductive substrate.

4. The biosensor of claim 1, wherein the capture probe comprises a nucleic acid, optionally, single-stranded DNA.

5. The biosensor of claim 1, wherein the capture probe is smaller than or equal to the target analyte in size, and/or the capture probe is smaller than or equal to the reporter moiety in size.

6. The biosensor of claim 1, wherein the target analyte comprises a nucleic acid, and/or wherein the reporter moiety comprises a nucleic acid.

7. The biosensor of claim 1, further comprising a surface blocker, optionally, monoethanolamine, mercaptohexanol and/or polyethylene glycol.

8. The biosensor of claim 1, wherein the conductive substrate comprises non-conductive glass or polymer and a conductive material, optionally the conductive material comprises indium tin oxide (ITO), fluorine-doped tin oxide (FTO), antimony-doped tin oxide (ATO), aluminum-doped zinc oxide (AZO), gallium-doped zinc oxide (GZO), indium-doped zinc oxide (IZO), or a combination thereof, and optionally the polymer comprises polyethylene terephthalate (PET), polyethylene naphthalate (PEN), polyimide (PI), or a combination thereof.

9. The biosensor of claim 1, wherein the photoactive material comprises thin films, photoactive particles, nanoparticles, microparticles, nanowires, nanorods, nanostars, nanomaterial, conductor materials, semiconductor materials, metals, metal oxides, carbon-based materials, conductive polymers, photoactive polymers, plasmonic materials, dyes, sulfide, metal chalcogenide, cadmium telluride, or a combination thereof.

10. The biosensor of claim 9, wherein the metal oxides are selected from the group consisting of Cd, Zn, In, Pb, Mo, W, Sb, Bi, Cu, Hg, Ti, Ag, Mn, Fe, V, Sn, Zr, Sr, Ga, Si, Cr, a perovskite such as $SrTiO_3$ or $CaTiO_3$, and a combination thereof, or wherein the metal chalcogenide is selected from the group consisting of CdSe, $In_2Se_3$, $WSe_2$, HgS, Pb Se, CdTe, and a combination thereof.

11. The biosensor of claim 1, wherein the photoactive material comprises titanium dioxide, zinc oxide, iron oxide, cadmium sulfide, cadmium telluride, or a combination thereof.

12. The biosensor of claim 1, wherein the photoactive material comprises titanium dioxide.

13. The biosensor of claim 12, wherein the titanium dioxide has a crystal structure that is at least one of anatase, rutile and brookite, optionally the titanium dioxide is P25-$TiO_2$.

14. The biosensor of claim 1, wherein the detectable label comprises a plasmonic nanoparticle, organic dye, light absorbing molecule, semiconductive nanoparticle, or a carbon-based nanomaterial.

15. The biosensor of claim 1, wherein the detectable label comprises a metal, semiconductive quantum dot or organic semiconductor.

16. The biosensor of claim 1, wherein the detectable label comprises a gold nanoparticle.

17. A method of detecting a target analyte in a sample, the method comprising:
  a) contacting the sample with the photoelectrode of the biosensor of claim 1 under conditions for binding the target analyte to a fraction of the population of capture probes functionalized on the photoelectrode, wherein the binding of the target analyte to a fraction of the population of capture probes results in a population of remaining unbound capture probes;
  b) measuring a detectable signal generated from a);
  c) introducing the reporter moiety to the photoelectrode of the biosensor of claim 1 under conditions for binding the reporter moiety to the remaining unbound capture probes; and
  d) measuring a detectable signal generated from c);
  wherein the binding of the target analyte to a fraction of the population of the capture probes in a) results in a decrease in the intensity of detection signal compared to the intensity of detection signal in the absence of any binding of the target analytes to the population of the capture probes;
  wherein in c) introducing the reporter moiety to the photoelectrode results in the binding of the reporter moiety to the population of remaining unbound capture probes which results in an increase in intensity in detection signal that is less than an increase in intensity in detection signal from binding of the reporter moiety to a population of capture probes that has not been exposed and not bound to the target analyte; and
  wherein a decrease in the signal intensity measured in b) from the capture probes binding the target analyte and an increase in the signal intensity measured in d) from the capture probes binding the reporter moiety indicates the presence of the target analyte in the sample.

18. The method of claim 17, wherein the detectable signal measured in b) is a change in photoelectrochemical current induced by the binding of the target analyte to the fraction of the population of the capture probes, and the detectable signal measured in d) is an additional change in photoelectrochemical current induced by the reporter moiety binding to the remaining unbound capture probes.

19. The method of claim 17, further comprising calculating a difference and/or ratio between the detectable signal measured in b) from the capture probes binding the target analyte and measured in d) from the capture probes binding the reporter moiety.

20. The method of claim 17, wherein the sample comprises tissue samples, urine, blood, serum, other bodily fluids and/or secretions.

* * * * *

UNITED STATES PATENT AND TRADEMARK OFFICE
CERTIFICATE OF CORRECTION

Page 1 of 1

PATENT NO. : 12,416,599 B2
APPLICATION NO. : 17/572376
DATED : September 16, 2025
INVENTOR(S) : Leyla Soleymani, Sudip Saha and Amanda Victorious It is certified that error appears in the above-identified patent and that said Letters Patent is hereby corrected as shown below:

In the Claims

Claim 10, Column 25, Line 18:
"Pb Se"
Should read:
-- PbSe --

Signed and Sealed this
Fourth Day of November, 2025

John A. Squires
*Director of the United States Patent and Trademark Office*